(12) United States Patent
Singh et al.

(10) Patent No.: US 10,285,734 B2
(45) Date of Patent: *May 14, 2019

(54) EXTERNAL FIXATOR SYSTEM

(71) Applicant: Stryker European Holdings I, LLC, Kalamazoo, MI (US)

(72) Inventors: Manoj Kumar Singh, Mahwah, NJ (US); Yves Stephane Crozet, Ramsey, NJ (US); Vinzenz Andreas Burgherr, Bern (CH); Mark Thomas Dahl, Afton, MN (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/137,677

(22) Filed: Sep. 21, 2018

(65) Prior Publication Data

US 2019/0021767 A1    Jan. 24, 2019

Related U.S. Application Data

(63) Continuation of application No. 16/108,787, filed on Aug. 22, 2018, which is a continuation of application (Continued)

(30) Foreign Application Priority Data

Aug. 11, 2010 (EP) .................................. 10172523
Aug. 4, 2011 (EP) .................................. 11176512

(51) Int. Cl.
*A61B 17/62* (2006.01)
*A61B 17/64* (2006.01)
(Continued)

(52) U.S. Cl.
CPC ............ *A61B 17/62* (2013.01); *A61B 17/645* (2013.01); *A61B 17/6425* (2013.01);
(Continued)

(58) Field of Classification Search
CPC ... A61B 17/62; A61B 17/6425; A61B 17/645; A61B 17/66; A61B 17/8875; A61H 3/00
(Continued)

(56) References Cited

U.S. PATENT DOCUMENTS 6,214 A     3/1849 Yerger
2,035,952 A 3/1936 Ettinger
(Continued)

FOREIGN PATENT DOCUMENTS

CA      2633944 A1  7/2007
CH      596826 A5   3/1978
(Continued)

OTHER PUBLICATIONS

Alizade et al., Mech. Mach. Theory, vol. 29, No. 1, pp. 115-124, 1994, Great Britain, © 1993.
(Continued)

*Primary Examiner* — Eduardo C Robert
*Assistant Examiner* — David C Comstock
(74) *Attorney, Agent, or Firm* — Lerner, David, Littenberg, Krumholz & Mentlik, LLP

(57) ABSTRACT

Disclosed herein are external fixation frames for correcting bone deformities. The external fixation frames include a top fixation ring and a bottom fixation ring coupled to one another by at least two struts. A half ring is coupled to bottom fixation ring. The bottom fixation ring is u-shaped. One or more rocker members may be coupled to the bottom fixation ring. The half ring may be hingedly coupled to the
(Continued)

bottom fixation ring such that it can rotate with respect to the bottom fixation ring from a first position to a second position.

20 Claims, 29 Drawing Sheets

Related U.S. Application Data

No. 15/635,960, filed on Jun. 28, 2017, now Pat. No. 10,080,585, which is a continuation of application No. 15/485,402, filed on Apr. 12, 2017, now Pat. No. 9,839,445, which is a continuation of application No. 14/707,630, filed on May 8, 2015, now Pat. No. 9,730,730, which is a continuation of application No. 14/564,675, filed on Dec. 9, 2014, now Pat. No. 9,220,533, which is a continuation of application No. 13/792,634, filed on Mar. 11, 2013, now Pat. No. 8,945,128, which is a continuation-in-part of application No. 13/206,058, filed on Aug. 9, 2011, now Pat. No. 8,834,467.

(51) Int. Cl.
*A61H 3/00* (2006.01)
*A61B 17/66* (2006.01)
*A61B 17/88* (2006.01)

(52) U.S. Cl.
CPC .............. *A61B 17/66* (2013.01); *A61H 3/00* (2013.01); *A61B 17/8875* (2013.01)

(58) Field of Classification Search
USPC ...................................................... 606/54–59
See application file for complete search history.

(56) References Cited

U.S. PATENT DOCUMENTS

| | | |
|---|---|---|
| 2,055,024 A | 9/1936 | Bittner |
| 2,291,747 A | 8/1942 | Neuwirth |
| 2,333,033 A | 10/1943 | Mraz |
| 2,391,537 A | 12/1945 | Anderson |
| 2,393,831 A | 1/1946 | Stader |
| 2,406,987 A | 9/1946 | Anderson |
| 2,883,219 A | 4/1959 | Cox |
| 3,691,788 A | 9/1972 | Mazziotti |
| 3,727,610 A | 4/1973 | Riniker |
| 3,863,037 A | 1/1975 | Schindler et al. |
| 3,941,123 A | 3/1976 | Volkov et al. |
| 3,977,397 A | 8/1976 | Kalnberz et al. |
| 3,985,127 A | 10/1976 | Volkov et al. |
| 4,006,740 A | 2/1977 | Volkov et al. |
| 4,100,919 A | 7/1978 | Oganesyan et al. |
| 4,127,119 A | 11/1978 | Kronner |
| 4,185,623 A | 1/1980 | Volkov et al. |
| 4,308,863 A | 1/1982 | Fischer |
| 4,338,927 A | 7/1982 | Volkov et al. |
| 4,365,624 A | 12/1982 | Jaquet |
| 4,403,606 A | 9/1983 | Woo et al. |
| 4,450,834 A | 5/1984 | Fischer |
| 4,520,983 A | 6/1985 | Templeman |
| 4,548,199 A | 10/1985 | Agee |
| 4,554,915 A | 11/1985 | Brumfield |
| 4,611,586 A | 9/1986 | Agee et al. |
| 4,615,338 A | 10/1986 | Ilizarov et al. |
| 4,730,608 A | 3/1988 | Schlein |
| 4,768,524 A | 9/1988 | Hardy |
| 4,784,125 A | 11/1988 | Monticelli et al. |
| 4,819,496 A | 4/1989 | Shelef |
| 4,889,111 A | 12/1989 | Ben-Dov |
| 4,905,680 A | 3/1990 | Tunc |
| 4,973,332 A | 11/1990 | Kummer |
| 4,976,582 A | 12/1990 | Clavel et al. |
| 4,978,348 A | 12/1990 | Ilizarov |
| 5,028,180 A | 7/1991 | Sheldon et al. |
| 5,062,844 A | 11/1991 | Jamison et al. |
| 5,067,954 A | 11/1991 | Ilizarov |
| 5,074,866 A | 12/1991 | Sherman et al. |
| 5,087,258 A | 2/1992 | Schewior |
| 5,112,331 A | 5/1992 | Miletich |
| 5,122,140 A | 6/1992 | Asche et al. |
| 5,160,335 A | 11/1992 | Wagenknecht |
| 5,179,525 A | 1/1993 | Griffis et al. |
| 5,207,676 A | 5/1993 | Canadell et al. |
| 5,275,598 A | 1/1994 | Cook |
| 5,279,176 A | 1/1994 | Tahmasebi et al. |
| 5,301,566 A | 4/1994 | Tahmasebi et al. |
| 5,353,504 A | 10/1994 | Pai |
| 5,358,504 A | 10/1994 | Paley et al. |
| 5,372,597 A | 12/1994 | Hotchkiss et al. |
| 5,391,167 A | 2/1995 | Pong et al. |
| 5,397,322 A | 3/1995 | Campopiano et al. |
| 5,437,666 A | 8/1995 | Tepic et al. |
| 5,451,225 A | 9/1995 | Ross, Jr. et al. |
| 5,466,237 A | 11/1995 | Byrd, III et al. |
| 5,496,319 A | 3/1996 | Allard et al. |
| 5,540,686 A | 7/1996 | Zippel et al. |
| 5,568,993 A | 10/1996 | Potzick |
| 5,630,814 A | 5/1997 | Ross, Jr. et al. |
| 5,658,283 A | 8/1997 | Huebner |
| 5,662,648 A | 9/1997 | Faccioli et al. |
| 5,681,309 A | 10/1997 | Ross, Jr. et al. |
| 5,688,271 A | 11/1997 | Faccioli et al. |
| 5,702,389 A | 12/1997 | Taylor et al. |
| 5,709,681 A | 1/1998 | Pennig |
| 5,713,897 A | 2/1998 | Goble et al. |
| 5,725,526 A | 3/1998 | Allard et al. |
| 5,725,527 A | 3/1998 | Biedermann et al. |
| 5,728,095 A | 3/1998 | Taylor et al. |
| 5,766,173 A | 6/1998 | Ross, Jr. et al. |
| 5,776,132 A | 7/1998 | Blyakher |
| 5,776,173 A | 7/1998 | Madsen, Jr. et al. |
| 5,779,703 A | 7/1998 | Benoist |
| 5,788,695 A | 8/1998 | Richardson |
| 5,797,908 A | 8/1998 | Meyers et al. |
| 5,843,081 A | 12/1998 | Richardson |
| 5,846,245 A | 12/1998 | McCarthy et al. |
| 5,863,292 A | 1/1999 | Tosic |
| 5,870,834 A | 2/1999 | Sheldon |
| 5,885,282 A | 3/1999 | Szabo |
| 5,891,143 A | 4/1999 | Taylor et al. |
| 5,897,555 A | 4/1999 | Clyburn et al. |
| 5,919,192 A | 7/1999 | Shouts |
| 5,921,985 A | 7/1999 | Ross, Jr. et al. |
| 5,928,230 A | 7/1999 | Tosic |
| 5,931,837 A | 8/1999 | Marsh et al. |
| 5,968,043 A | 10/1999 | Ross, Jr. et al. |
| 5,971,984 A | 10/1999 | Taylor et al. |
| 5,976,133 A | 11/1999 | Kraus et al. |
| 5,997,537 A | 12/1999 | Walulik |
| 6,007,535 A | 12/1999 | Rayhack et al. |
| 6,010,501 A | 1/2000 | Raskin et al. |
| 6,013,081 A | 1/2000 | Burkinshaw et al. |
| 6,021,579 A | 2/2000 | Schimmels et al. |
| 6,030,386 A | 2/2000 | Taylor et al. |
| 6,036,691 A | 3/2000 | Richardson |
| 6,086,283 A | 7/2000 | Ziegert |
| 6,090,111 A | 7/2000 | Nichols |
| 6,099,217 A | 8/2000 | Wiegand et al. |
| 6,129,727 A | 10/2000 | Austin et al. |
| 6,176,860 B1 | 1/2001 | Howard |
| 6,196,081 B1 | 3/2001 | Yau |
| 6,245,071 B1 | 6/2001 | Pierson |
| 6,277,118 B1 | 8/2001 | Grant et al. |
| 6,328,737 B1 | 12/2001 | Moorcroft et al. |
| 6,342,052 B1 | 1/2002 | Allende |
| 6,342,054 B1 | 1/2002 | Mata |
| 6,355,037 B1 | 3/2002 | Crosslin et al. |
| 6,371,957 B1 | 4/2002 | Amrein et al. |
| 6,391,250 B1 | 5/2002 | Wolfsgruber et al. |
| 6,423,061 B1 | 7/2002 | Bryant |

(56) References Cited

U.S. PATENT DOCUMENTS

| | | |
|---|---|---|
| 6,428,540 B1 | 8/2002 | Claes et al. |
| 6,491,694 B1 | 12/2002 | Orsak |
| 6,537,275 B2 | 3/2003 | Venturini et al. |
| 6,565,565 B1 | 5/2003 | Yuan et al. |
| 6,565,567 B1 | 5/2003 | Haider |
| 6,610,063 B2 | 8/2003 | Kumar et al. |
| 6,613,049 B2 | 9/2003 | Winquist et al. |
| 6,648,583 B1 | 11/2003 | Roy et al. |
| 6,648,891 B2 | 11/2003 | Kim |
| 6,652,524 B1 | 11/2003 | Weiner |
| 6,671,975 B2 | 1/2004 | Hennessey |
| 6,701,174 B1 | 3/2004 | Krause et al. |
| 6,733,502 B2 | 5/2004 | Altarac et al. |
| 6,746,448 B2 | 6/2004 | Weiner et al. |
| 6,769,194 B2 | 8/2004 | Hennessey |
| 6,784,125 B1 | 8/2004 | Yamakawa et al. |
| 6,793,655 B2 | 9/2004 | Orsak |
| 6,860,883 B2 | 3/2005 | Janowski et al. |
| 6,964,663 B2 | 11/2005 | Grant et al. |
| 7,022,122 B2 | 4/2006 | Amreim et al. |
| 7,048,735 B2 | 5/2006 | Ferrante et al. |
| 7,127,660 B2 | 10/2006 | Blaum |
| 7,147,640 B2 | 12/2006 | Huebner et al. |
| 7,197,806 B2 | 4/2007 | Boudreaux et al. |
| 7,226,449 B2 | 6/2007 | Venturini et al. |
| 7,261,713 B2 | 8/2007 | Langmaid et al. |
| 7,276,069 B2 | 10/2007 | Biedermann et al. |
| 7,282,052 B2 | 10/2007 | Mullaney |
| 7,291,148 B2 | 11/2007 | Agee et al. |
| 7,306,601 B2 | 12/2007 | McGrath et al. |
| 7,311,711 B2 | 12/2007 | Cole |
| 7,361,176 B2 | 4/2008 | Cooper et al. |
| 7,377,923 B2 | 5/2008 | Purcell et al. |
| 7,422,593 B2 | 9/2008 | Cresina et al. |
| 7,449,023 B2 | 11/2008 | Walulik et al. |
| 7,468,063 B2 | 12/2008 | Walulik et al. |
| 7,479,142 B2 | 1/2009 | Weiner et al. |
| 7,491,008 B2 | 2/2009 | Thomke et al. |
| 7,507,240 B2 | 3/2009 | Olsen |
| 7,527,626 B2 | 5/2009 | Lutz et al. |
| 7,575,575 B2 | 8/2009 | Olsen et al. |
| 7,578,822 B2 | 8/2009 | Rezach et al. |
| RE40,914 E | 9/2009 | Taylor et al. |
| 7,608,074 B2 | 10/2009 | Austin et al. |
| 7,632,271 B2 | 12/2009 | Baumgartner et al. |
| 7,699,848 B2 | 4/2010 | Hoffman et al. |
| 7,708,736 B2 | 5/2010 | Mullaney |
| 7,749,224 B2 | 7/2010 | Cresina et al. |
| 7,763,020 B2 | 7/2010 | Draper |
| 7,803,158 B2 | 9/2010 | Hayden |
| 7,806,843 B2 | 10/2010 | Marin |
| 7,815,586 B2 | 10/2010 | Grant et al. |
| 7,875,030 B2 | 1/2011 | Hoffmann-Clair et al. |
| 7,881,771 B2 | 2/2011 | Koo et al. |
| 7,887,498 B2 | 2/2011 | Marin |
| 7,887,537 B2 | 2/2011 | Ferrante et al. |
| 7,931,650 B2 | 4/2011 | Winquist et al. |
| 7,938,829 B2 | 5/2011 | Mullaney |
| 7,955,333 B2 | 6/2011 | Yeager |
| 7,955,334 B2 | 6/2011 | Steiner et al. |
| 7,985,221 B2 | 7/2011 | Coull et al. |
| 8,029,505 B2 | 10/2011 | Hearn et al. |
| 8,057,474 B2 | 11/2011 | Knuchel et al. |
| 8,114,077 B2 | 2/2012 | Steiner et al. |
| 8,137,347 B2 | 3/2012 | Weiner et al. |
| 8,142,432 B2 | 3/2012 | Matityahu |
| 8,147,490 B2 | 4/2012 | Bauer |
| 8,147,491 B2 | 4/2012 | Lavi |
| 8,157,800 B2 | 4/2012 | Vvedensky et al. |
| 8,172,849 B2 | 5/2012 | Noon et al. |
| 8,182,483 B2 | 5/2012 | Bagnasco et al. |
| 8,187,274 B2 | 5/2012 | Schulze |
| 8,192,434 B2 | 6/2012 | Huebner et al. |
| 8,202,273 B2 | 6/2012 | Karidis |
| 8,241,285 B2 | 8/2012 | Mullaney |
| 8,251,937 B2 | 8/2012 | Marin |
| 8,257,353 B2 | 9/2012 | Wong et al. |
| 8,282,652 B2 | 10/2012 | Mackenzi et al. |
| 8,858,555 B2 | 10/2014 | Crozet et al. |
| 8,906,020 B2 | 12/2014 | Crozet et al. |
| 8,945,128 B2 * | 2/2015 | Singh .................... A61B 17/62 606/54 |
| 8,951,252 B2 | 2/2015 | Steiner et al. |
| 9,668,794 B2 | 6/2017 | Kuster et al. |
| 9,730,730 B2 * | 8/2017 | Singh .................... A61B 17/62 |
| 9,839,445 B2 * | 12/2017 | Singh .................... A61B 17/62 |
| 2001/0025181 A1 | 9/2001 | Freedlan |
| 2001/0049526 A1 | 12/2001 | Venturini et al. |
| 2002/0010465 A1 | 1/2002 | Koo et al. |
| 2002/0013584 A1 | 1/2002 | Termaten |
| 2002/0042613 A1 | 4/2002 | Mata |
| 2002/0165543 A1 | 11/2002 | Winquist et al. |
| 2003/0063949 A1 | 4/2003 | Hohenocker |
| 2003/0069580 A1 | 4/2003 | Langmaid et al. |
| 2003/0106230 A1 | 6/2003 | Hennessey |
| 2003/0109879 A1 | 6/2003 | Orsak |
| 2003/0181911 A1 | 9/2003 | Venturini |
| 2003/0191466 A1 | 10/2003 | Austin et al. |
| 2003/0216734 A1 | 11/2003 | Mingozzi et al. |
| 2003/0225406 A1 | 12/2003 | Weiner et al. |
| 2004/0059331 A1 | 3/2004 | Mullaney |
| 2004/0073211 A1 | 4/2004 | Austin et al. |
| 2004/0073212 A1 | 4/2004 | Kim |
| 2004/0097944 A1 | 5/2004 | Koman et al. |
| 2004/0116926 A1 | 6/2004 | Venturini et al. |
| 2004/0133199 A1 | 7/2004 | Coati et al. |
| 2004/0133200 A1 | 7/2004 | Ruch et al. |
| 2004/0167518 A1 | 8/2004 | Estrada |
| 2005/0015087 A1 | 1/2005 | Walulik et al. |
| 2005/0043730 A1 | 2/2005 | Janowski et al. |
| 2005/0059968 A1 | 3/2005 | Grant et al. |
| 2005/0084325 A1 | 4/2005 | O'Brien et al. |
| 2005/0113829 A1 | 5/2005 | Walulik et al. |
| 2005/0119656 A1 | 6/2005 | Ferrante et al. |
| 2005/0149018 A1 | 7/2005 | Cooper et al. |
| 2005/0215997 A1 | 9/2005 | Austin et al. |
| 2005/0234448 A1 | 10/2005 | McCarthy |
| 2005/0248156 A1 | 11/2005 | Hsieh |
| 2005/0251136 A1 | 11/2005 | Noon et al. |
| 2006/0155276 A1 | 7/2006 | Walulik et al. |
| 2006/0184169 A1 | 8/2006 | Stevens |
| 2006/0229605 A1 | 10/2006 | Olsen |
| 2006/0235383 A1 | 10/2006 | Hollawell |
| 2006/0243873 A1 | 11/2006 | Carnevali |
| 2006/0247622 A1 | 11/2006 | Maughan et al. |
| 2006/0247629 A1 | 11/2006 | Maughan et al. |
| 2006/0261221 A1 | 11/2006 | Carnevali |
| 2006/0276786 A1 | 12/2006 | Brinker |
| 2006/0287652 A1 | 12/2006 | Lessig et al. |
| 2007/0038217 A1 | 2/2007 | Brown et al. |
| 2007/0043354 A1 | 2/2007 | Koo et al. |
| 2007/0049930 A1 | 3/2007 | Hearn et al. |
| 2007/0055233 A1 | 3/2007 | Brinker |
| 2007/0055234 A1 | 3/2007 | McGrath et al. |
| 2007/0123857 A1 | 5/2007 | Deffenbaugh et al. |
| 2007/0161983 A1 | 7/2007 | Cresina et al. |
| 2007/0161984 A1 | 7/2007 | Cresina et al. |
| 2007/0162022 A1 | 7/2007 | Zhang et al. |
| 2007/0225704 A1 | 9/2007 | Ziran et al. |
| 2007/0233061 A1 | 10/2007 | Lehmann et al. |
| 2007/0250071 A1 | 10/2007 | Soerensen et al. |
| 2007/0255280 A1 | 11/2007 | Austin et al. |
| 2007/0282338 A1 | 12/2007 | Mullaney |
| 2008/0021451 A1 | 1/2008 | Coull et al. |
| 2008/0021452 A1 | 1/2008 | Ducharme et al. |
| 2008/0154310 A1 | 6/2008 | White et al. |
| 2008/0228185 A1 | 9/2008 | Vasta et al. |
| 2008/0269741 A1 | 10/2008 | Karidis |
| 2009/0018541 A1 | 1/2009 | Lavi |
| 2009/0036890 A1 | 2/2009 | Karidis |
| 2009/0036891 A1 | 2/2009 | Brown et al. |
| 2009/0105621 A1 | 4/2009 | Boyd et al. |
| 2009/0131935 A1 | 5/2009 | Yeager |
| 2009/0157088 A1 | 6/2009 | Mengato |

(56) References Cited

U.S. PATENT DOCUMENTS

| | | |
|---|---|---|
| 2009/0177198 A1 | 7/2009 | Theodoros et al. |
| 2009/0198234 A1 | 8/2009 | Knuchel et al. |
| 2009/0198235 A1 | 8/2009 | Steiner et al. |
| 2009/0264882 A1 | 10/2009 | Steiner et al. |
| 2009/0264883 A1 | 10/2009 | Steiner et al. |
| 2009/0287212 A1 | 11/2009 | Hirata et al. |
| 2009/0312757 A1 | 12/2009 | Kehres et al. |
| 2010/0087819 A1 | 4/2010 | Mullaney |
| 2010/0145336 A1 | 6/2010 | Draper |
| 2010/0179548 A1 | 7/2010 | Marin |
| 2010/0191239 A1 | 7/2010 | Sakkers et al. |
| 2010/0234844 A1 | 9/2010 | Edelhauser et al. |
| 2010/0249779 A1 | 9/2010 | Hotchkiss et al. |
| 2010/0280516 A1 | 11/2010 | Taylor |
| 2010/0298827 A1 | 11/2010 | Cremer et al. |
| 2010/0305568 A1 | 12/2010 | Ross et al. |
| 2010/0312243 A1 | 12/2010 | Ross et al. |
| 2010/0331840 A1 | 12/2010 | Ross et al. |
| 2011/0060336 A1 | 3/2011 | Pool et al. |
| 2011/0066151 A1 | 3/2011 | Murner et al. |
| 2011/0082458 A1 | 4/2011 | Crozet et al. |
| 2011/0098707 A1 | 4/2011 | Mullaney |
| 2011/0112533 A1 | 5/2011 | Venturini et al. |
| 2011/0118737 A1 | 5/2011 | Vasta et al. |
| 2011/0118738 A1 | 5/2011 | Vasta et al. |
| 2011/0172663 A1 | 7/2011 | Mullaney |
| 2011/0172664 A1 | 7/2011 | Bagnasco et al. |
| 2011/0208187 A1 | 8/2011 | Wong et al. |
| 2011/0245830 A1 | 10/2011 | Zgonis et al. |
| 2011/0288549 A1 | 11/2011 | Steiner et al. |
| 2011/0313418 A1 | 12/2011 | Nikonovas |
| 2011/0313419 A1 | 12/2011 | Mullaney |
| 2012/0004659 A1 | 1/2012 | Miller et al. |
| 2012/0041439 A1 | 2/2012 | Singh et al. |
| 2012/0078251 A1 | 3/2012 | Benenati et al. |
| 2012/0089142 A1 | 4/2012 | Mullaney et al. |
| 2012/0095462 A1 | 4/2012 | Miller |
| 2012/0136355 A1 | 5/2012 | Wolfson |
| 2012/0143190 A1 | 6/2012 | Wolfson |
| 2013/0253512 A1 | 9/2013 | Crozet et al. |
| 2014/0378972 A1 | 12/2014 | Crozet et al. |

FOREIGN PATENT DOCUMENTS

| | | |
|---|---|---|
| DE | 3114455 A1 | 10/1982 |
| DE | 4421223 A1 | 12/1995 |
| DE | 202006006734 U1 | 6/2006 |
| EP | 0377744 A1 | 7/1990 |
| EP | 611007 A1 | 8/1994 |
| EP | 1016381 A1 | 7/2000 |
| EP | 1136041 A2 | 9/2001 |
| EP | 03/086213 | 10/2003 |
| EP | 2417923 A1 | 2/2012 |
| EP | 2417924 A1 | 2/2012 |
| FR | 2439002 A1 | 5/1980 |
| FR | 2576774 A1 | 8/1986 |
| FR | 2756025 A1 | 5/1998 |
| GB | 2250682 A | 6/1992 |
| IT | 1259768 B | 3/1996 |
| WO | 92/14426 | 9/1992 |
| WO | 9418898 A1 | 9/1994 |
| WO | 97/30650 | 8/1997 |
| WO | 97/30651 | 8/1997 |
| WO | 01/15611 A1 | 3/2001 |
| WO | 01/22892 A1 | 4/2001 |
| WO | 01/78613 | 10/2001 |
| WO | 2006116307 | 11/2006 |
| WO | 2007067297 A2 | 6/2007 |
| WO | 2007075114 | 7/2007 |
| WO | 2007111576 A2 | 10/2007 |
| WO | 2009100459 A1 | 8/2009 |
| WO | 2010104567 A1 | 9/2010 |
| WO | 2011060266 A1 | 5/2011 |
| WO | 2012102685 A1 | 8/2012 |

OTHER PUBLICATIONS

Basic Ilizarov Techniques, Techniques in Orthopaedics, vol. 5, No. 4, pp. 55-59, Dec. 1990.
BIOMET® Vision™ Footring™ System: Surgical Technique, 39 pages, (2008).
Crozet et al., U.S. Appl. No. 13/788,466, filed Mar. 7, 2013, titled "Dynamic External Fixator and Methods for Use".
European Search Report for Application No. EP15167691 dated Sep. 17, 2015.
European Search Report, EP 08 15 0944 dated Aug. 18, 2008.
European Search Report, EP 08 15 0960 dated Jul. 30, 2008.
European Search Report, EP 08 15 4754 dated Jul. 4, 2008.
European Search Report, EP 08 15 4761 dated Aug. 21, 2008.
European Search Report, EP 10 172 523 dated Mar. 25, 2011.
European Search Report, EP 11176512, dated Sep. 19, 2011.
European Search Report, EP 11176566, dated Sep. 20, 2011.
Extended European Search Report EP16170790, dated Dec. 19, 2016, 5 pages.
Extended European Search Report for Application No. EP13180720 dated Apr. 15, 2014.
Extended European Search Report for Application No. EP14154811 dated Jun. 30, 2014.
Extended European Search Report for Application No. EP14158464 dated Jul. 3, 2014.
Hwang et al, Asian Journal of Control, vol. 6, No. 1, pp. 136-144, Mar. 2004.
International Search Report and Written Opinion, PCT/US2010/000712, dated Jun. 28, 2010.
Nanua et al., IEEE Transactions on Robotics and Automation, vol. 6, No. 4, pp. 438-444, Aug. 1990.
Partial European Search Report for Application No. EP13180720 dated Dec. 3, 2013.
S.V. Sreenivasan et al., "Closed-Form Direct Displacement Analysis of a 6-6 Stewart Platform," Mech. Mach. Theory, vol. 29, No. 6, pp. 855-864, 1994.
Smith&Nephew, Taylor Spatial Frame, website printout, Aug. 12, 2009.
Taylor et al., U.S. Appl. No. 09/827,252, filed Apr. 5, 2001, titled "Orthopaedic Fixation Plate".
Tibiotalocalcaneal Arthrodesis with the ILIZAROV method, Surgical Technique, ILIZAROV Foot and Ankle External Fixation, Smith & Nephew, Inc., May 2010.
U.S. Appl. No. 13/592,832, filed Aug. 23, 2013 (not yet published).

\* cited by examiner

EXTERNAL FIXATOR SYSTEM

CROSS-REFERENCE TO RELATED APPLICATIONS

The present application is continuation of U.S. patent application Ser. No. 16/108,787, filed Aug. 22, 2018, which is a continuation of U.S. patent application Ser. No. 15/635,960, filed Jun. 28, 2017, which is a continuation of U.S. Pat. No. 9,839,445, filed Apr. 12, 2017, which is a continuation of U.S. Pat. No. 9,730,730, filed May 8, 2015, which is a continuation of U.S. Pat. No. 9,220,533, filed Dec. 9, 2014, which is a continuation of U.S. Pat. No. 8,945,128, filed Mar. 11, 2013, which is a continuation-in-part of U.S. Pat. No. 8,834,467, filed Aug. 9, 2011, which claims priority to European Application No. 10 172 523.2, filed Aug. 11, 2010, and European Application No. 11 176 512.9, filed Aug. 4, 2011. The disclosures of each of the above-referenced applications are hereby incorporated by reference herein.

FIELD OF THE INVENTION

The present disclosure relates to an external fixation frame for correcting a bone deformity. More particularly, the present disclosure relates to an external fixation frame having an arch or half-ring connected to a bottom fixation ring of the external fixation frame.

BACKGROUND OF THE INVENTION

Many different types of bone deformities can be corrected using external fixation systems to perform the distraction osteogenesis process. For example, an Ilizarov device or similar external fixation system may be used. Such systems generally use rings also designated as fixation plates connected by threaded rods or struts with nuts for manipulation, angulation, and translation of the length discrepancies of bones. The nuts that are used to adjust the length of the struts are generally manually adjusted by a surgeon or by the patient with a wrench or by hand to change the positions of the rings and/or percutaneous fixation components.

As the position adjustments of the components are made where the nuts are secured, it can be difficult for the patient, for example, to make the required daily adjustments with consideration of maintaining stable fixation. Other devices use different techniques to adjust the effective length of the struts or rods but all must be adjusted somewhere between the ends thereof. The devices generally offer limited access for the patient. Because the adjustments are often a daily task for the patient, easier access to the frame adjustment points would be a significant advantage.

Fixation systems, especially foot fixation systems, have many areas of needed improvement. For example, existing foot fixation products on the market are static and do not allow for adjustment and pivoting. Certain foot fixation systems include a solid and stationary half-ring assembled to the foot ring. This lack of flexibility and motion restricts the motion of the foot and ankle and the external fixation frame during deformity correction, making the process more difficult for the physician and the patient and potentially preventing an optimal clinical outcome.

To allow for deformity correction of the foot and ankle, an adjustable and pivoting component that can be assembled onto the distal portion of a foot ring of an external fixation frame is needed.

BRIEF SUMMARY OF THE INVENTION

In one embodiment, an external fixation frame for correcting a bone deformity includes a first and second fixation ring. A posterior adjustable length strut couples a posterior portion of the first fixation ring to a posterior portion of the second fixation ring, the posterior adjustable length strut including a universal joint at an end thereof. Medial and lateral adjustable length struts couple medial and lateral portions of the first fixation ring to medial and lateral portions of the second fixation ring, respectively. The medial and lateral adjustable length struts include a constrained hinge joint at ends thereof. A half ring is hingedly coupled to the second fixation ring and an anterior adjustable length strut couples an anterior portion of the first fixation ring to the half ring.

The half ring may include a lateral end portion, a medial end portion, and an arcuate body portion connecting the lateral end portion to the medial end portion. The medial end portion of the half ring includes a first constrained hinge joint and the lateral end portion of the half ring includes a second constrained hinge joint. The second fixation ring may be U-shaped and include a medial anterior projection, a lateral anterior projection, and a rounded posterior section connecting the medial anterior projection to the lateral anterior projection. The first constrained hinge joint may couple the medial end portion of the half ring to the medial anterior projection of the second fixation ring and the second constrained hinge joint may couple the lateral end portion of the half ring to the lateral anterior projection of the second fixation ring.

The anterior adjustable length strut may include a distal constrained hinge joint and a proximal universal hinge joint. The distal constrained hinge joint of the anterior adjustable length strut may be coupled to the arcuate body portion of the half ring and the proximal universal hinge joint of the anterior adjustable length strut may be coupled to the anterior portion of the first fixation ring. The medial adjustable length strut and lateral adjustable length strut may each include an aperture proximal of the constrained hinge joint, each aperture being configured to accept a wire fastener therethrough. The half ring may include an aperture with a diameter and the anterior adjustable length strut may include a connecting element at a distal end thereof. The connecting element may include internal threading on the distal end of the strut and an externally threaded bolt, a portion of the bolt having a diameter greater than the diameter of the half ring aperture.

The external fixation frame may also include a rocker member coupled to a bottom surface of the second fixation ring. The rocker member may include a curved body portion with at least one connecting element projecting proximally from the curved body portion and configured to mate with an aperture in the second fixation ring. The connecting element may include a main body portion extending through an aperture in the curved body portion of the rocker member and a distal flange. The distal flange may extend distally of the main portion and be configured to contact a corresponding shoulder portion of the aperture in the curved body portion. The rocker member may further include a ground-contacting rounded distal portion coupled to a distal portion of the curved body portion of the rocker member, the ground-contacting rounded distal portion having a textured ground-contacting surface.

In another embodiment, an external fixation frame for correcting a bone deformity may include a first and second fixation ring. The second fixation ring may have a first free end, a second free end, and an arcuate portion connecting the first free end to the second free end. At least four struts couple the first fixation ring to the second fixation ring. At least one bone fastener has a first end operably coupled to the first free end of the second fixation ring and a second end operably coupled to the second free end of the second fixation ring. A half ring has a first free end, a second free end, and an arcuate portion connecting the first free end to the second free end. The first free end of the half ring is coupled to the first free end of the second fixation ring and the second free end of the half ring is coupled to the second free end of the second fixation ring. The bone fastener may be a K-wire. The external fixation frame may also include a first compression module coupled to the first free end of the second fixation ring and a second compression module coupled to the second free end of the second fixation ring. The first end of the bone fastener may be coupled to the first compression module and the second end of the bone fastener may be coupled to the second compression module.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same.

A more complete appreciation of the subject matter of the present invention and the various advantages thereof can be realized by reference to the following detailed description in which reference is made to the accompanying drawings in which.

DETAILED DESCRIPTION

Figure 1A:
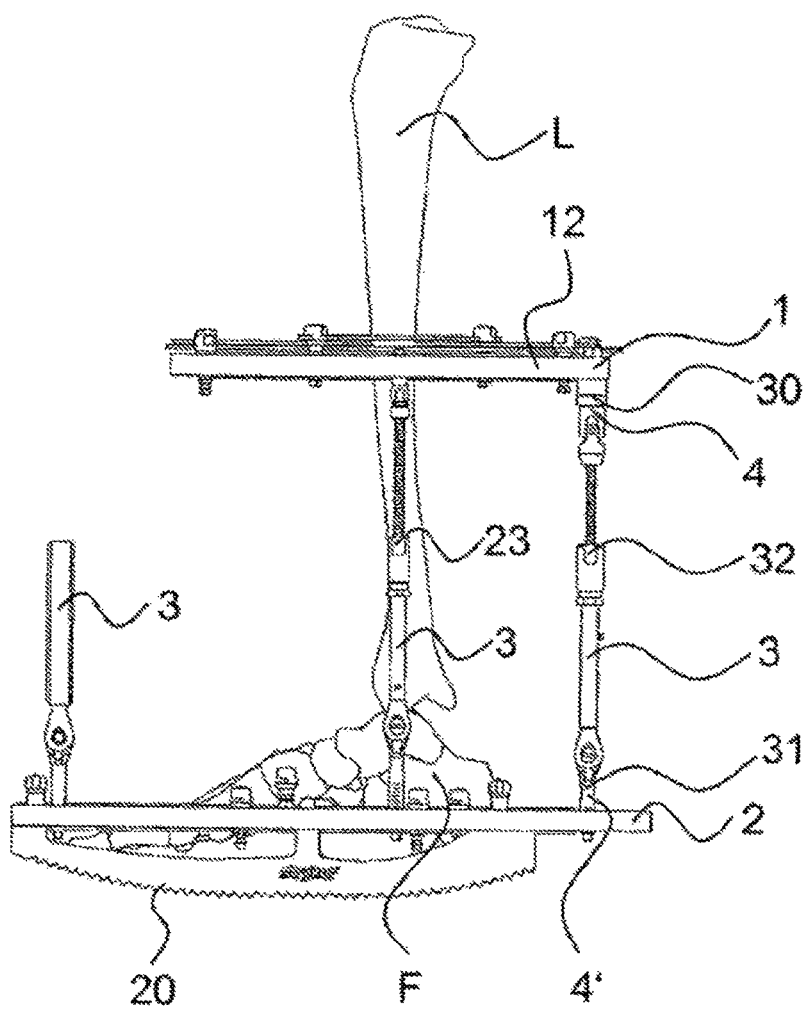
FIGS. 1A-C show side views of different strut configurations of an external fixator system of the present invention with first and second plates coupled to a tibia and a foot of a patient respectively.

As used herein, the term "proximal" means a direction closer to the heart of a patient and the term "distal" means a direction farther away from the heart of a patient. The term "anterior" means towards the front part of the body or the face and the term "posterior" means towards the back of the body. The term "medial" means toward the midline of the body and the term "lateral" means away from the midline of the body.

Referring to FIGS. 1-6, there is shown an embodiment of an external fixator system of the present invention. As shown in those figures, the external fixator system includes first and second fixation plates 1, 2 coupled to first and second bone segments L, F respectively, a plurality of adjustable length struts 3, at least one actuation unit 4, and a plurality of clamping units 4'.

FIGS. 1A-E show an exemplary embodiment of an external fixator system. The external fixator system comprises at least two fixation plates 1, 2 which are arranged at a distance to each other and at least one adjustable length strut 3 which is in connection with the fixation plates 1, 2. Such struts are shown in U.S. Publications 200910198234 and 200910198235 the disclosures of which are incorporated herein by reference in their entirety. Fixation plates 1, 2 serve as bearing elements for pins which are in connection with bony structure such as first and second bone segments L, F, for example. The orientation as well as the distance between two fixation plates 1, 2 thereby define the orientation and distance between fractured elements of the bony structure. Each of the fixation plates 1, 2 comprises a front surface 12 which extends over the largest dimension of the plate 1, 2.

In the present embodiment there is an upper fixation plate 1 in connection with the lower leg L and a lower fixation plate 2 in connection with the foot F. The lower fixation plate 2 comprises also a rolling structure 20 to enable a user to walk around.

Adjustable length struts 3 each include a length adjusting mechanism 32 having a threaded strut 33 and a non-rotating strut 34 having an internal thread along at least a portion of a length thereof in which the threaded strut 33 engages. Struts 3 include a first end region 30 and a second end region 31 in which the struts 3 are coupled to the respective fixation plates. In the present embodiment the struts 3 are connected to the upper fixation plate 1 by means of an actuation unit 4 and to the lower fixation plate 2 by means of a clamping element 4'. It is also possible to use an actuation unit 4 to connect the strut 3 to the upper fixation plate 1 as well as to the lower fixation plate 2. The actuation unit 4 is preferably provided to actuate the length-adjusting strut in order to adjust its length.

The actuation unit 4 is preferably in a fixed connection with fixation plates 1, 2 as shown in FIGS. 1A-E. The term fixed connection is to be understood as being a connection which prevents unintentional relative motion between the actuation unit 4 and fixation plates 1, 2. In particular, a rotational motion is preferably prevented. Preferably, fixation plates 1, 2 comprise a plurality of openings 10 in which such actuation units 4 can be arranged and such that the fixed connection can be established. The fixed connection has the advantage such that the device can be adjusted easily without the aid of several tools.

Figure 2:
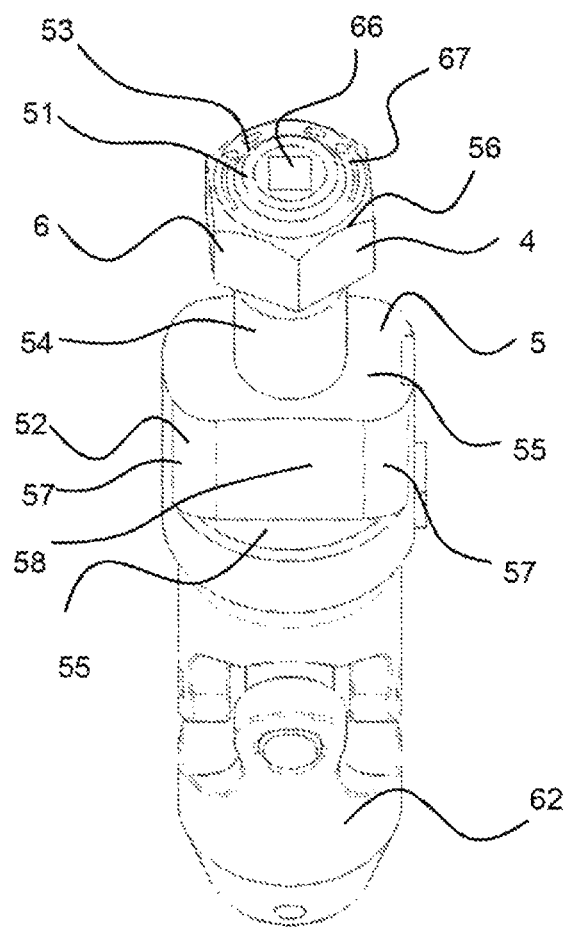
FIG. 2 shows an embodiment of an actuation unit of the present invention used in the external fixator system of FIGS. 1A-C.
Figure 3:
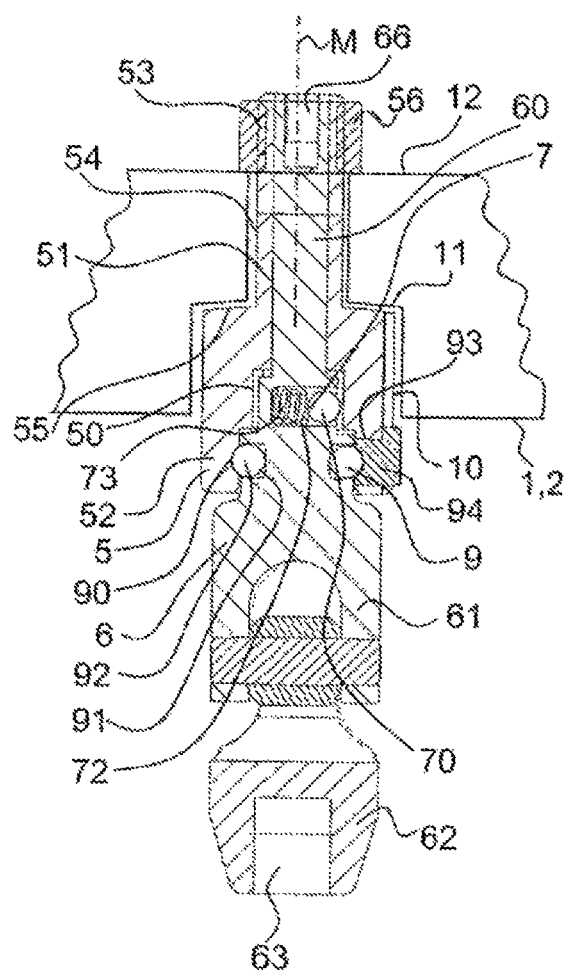
FIG. 3 shows a cross-sectional view of the actuation unit of FIG. 2.
Figure 4:
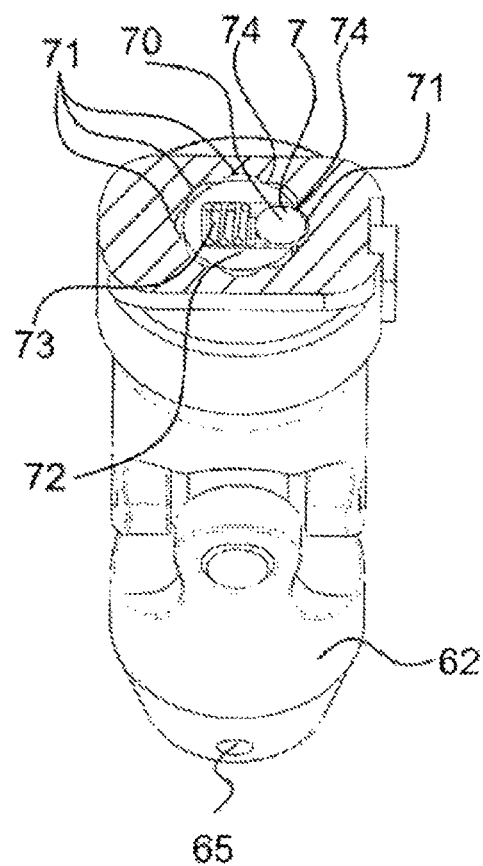
FIG. 4 shows a perspective partial cross-sectional view of the actuation unit of FIG. 3.

FIG. 2 shows the actuation unit 4 in a perspective view and FIGS. 3 and 4 show sectional views. The actuation unit 4 comprises an outer sleeve 5 in which an actuation element 6 is arranged. The actuation unit 4 is in connection with the fixation plate 1, 2 by means of the outer sleeve 5. Outer sleeve 5 is shown having a partly round configuration but may have other configurations such as rectangular, spherical, square and the like.

The outer sleeve 5 extends along a middle axis M as shown in FIG. 3 and comprises a through opening 50, a clamping section 51 and a bearing section 52. The clamping section 51 includes a threaded section 53 and a shaft section 54. The threaded section is in contact with a nut 56 which is used to secure the outer sleeve 5 to the fixation plate 1, 2. On the outer side a flange 55 divides the clamping section 51 from the bearing section 52. The bearing section 52 has mainly two purposes, namely to bear the actuation element and to provide a bearing of the outer sleeve 5 in the opening 10. Hence the inner side provided by said through opening 50 serves to provide a bearing for an actuation element 6 of actuation unit 4. The outer side of the bearing section 52 serves mainly to provide a bearing for the outer sleeve 5 within said opening 10 in the ring 1 as explained below with regard to FIG. 3 in more detail. The outer side of the bearing section 52 has in the present embodiment a rectangular cross section with rounded edges 57 and flat sidewalls 58. Edges 57 and sidewalls 58 extend parallel to the middle axis M. The part which is located in vicinity of flange 55, however, is preferably also in connection with the opening in the fixation plate 1, 2.

In FIG. 3, one embodiment of an opening 10 in the fixation plate 1, 2 is schematically shown. The opening 10 comprises a shoulder 11 which subdivides the opening 10. The opening 10 comprises a first section 13 and a second section 14. The shoulder 11 is located between the first section 13 and the second section 14. The first section 13 of the opening 10 has therefore a complementary or corresponding shape as the shaft section 54. In the present embodiment shaft section 54 as well as first section 13 have circular cross-sections and the second section 14 as well as the bearing section 52 have a rectangular cross-section.

When the outer sleeve 5 is inserted into the opening 10 the shoulder 11 is preferably in contact with flange 55. The shaft section 54 of the outer sleeve 5 extends through the first section 13 of the opening 10 and the bearing section 52 extends into the section 14. The outer sleeve 5 is fixed to the fixation plate 1, 2 by means of nut 56 which retracts the outer sleeve 55 relative to fixation plate 1, 2 such that flange 55 comes in contact with the shoulder 11.

From FIG. 2 it becomes evident that the cross-section of the outer surface of the bearing section 52 which is in contact with the opening 10 is provided such that rotation of outer sleeve 5 relative to the fixation plate 1, 2 is prevented. For that reason the opening 10 has a complementary shape. In the present embodiment, the outer sleeve 5 has partly a rectangular cross-section with rounded edges. Here the rectangular cross-section is mainly provided by the outer side of the bearing section 52 or the outer surfaces of the bearing section 52, respectively.

The actuation element 6 of actuation unit 4 preferably extends along the middle axis M and comprises mainly a shaft section 60 which extends through the opening 50 of the outer sleeve and a connection section 61 which is in connection with strut 3. The actuation element 6 can be actuated, i.e. rotated, by means of a tool 67 shown in FIG. 5, which preferably engages in a socket 66 of the actuation element 6. Socket 66 is thereby arranged such that the tool can be introduced in a direction which is more or less in line with the axis of the strut or in a direction perpendicular to the fixation plate 1, 2 in particular to surface 12. The orientation of the socket 66 has thereby the advantage that easy access is provided from the top of the fixation system and that the length of the struts 3 can be adjusted easily by any user of the system.

The actuation element 6 is borne by means of a ball bearing 9 in the outer sleeve 5. In the present embodiment, the ball bearing 9 is provided by means of the shaft section 61 and the bearing section 52. A separate ball bearing is also possible, but a ball bearing which is provided according to the embodiment of FIG. 3 is preferably compact in terms of size.

As shown in FIG. 3, the bearing section 52 and the shaft section 61 preferably comprise respective grooves 90, 91 in which a plurality of balls 92 are arranged. Groove 90 extends into the surface of the opening 50 and encompasses the whole opening 50, whereas groove 91 is arranged in the shaft 61 of the actuation element 6. The grooves 90, 91 provide a channel in which the balls 92 are arranged. Balls 92 may be introduced into the channel via an opening 93 in the shaft section 61 which is covered by means of a cover 94.

Between the outer sleeve 5 and the actuation element 6 there is arranged a feedback unit 7 as shown in FIGS. 3 and 4. In the present embodiment, the feedback unit 7 is provided by means of a spring-loaded ball 70 and corresponding chambers 71. The spring-loaded ball 70 is arranged in an opening 72 in the actuation element 6. Between the ground of the opening 72 and the spring-loaded ball 70 there is arranged a spring 73 which provides a force that pushes the ball 70 into a respective chamber 71. The chambers 71 are arranged in the surface of the through opening 50 in the outer sleeve 5. Upon rotation of the actuation element 6 relative to the outer sleeve 5, the spring-loaded ball 70 is pushed against the spring force by means of the transition portion 74 between two neighboring chambers 71. As soon as the next chamber 71 is in line with the spring axis, the spring-loaded ball 70 will be moved into the respective chamber 71. This mechanism results in a clicking noise which provides the user with a respective audible feedback about the amount of actuation that is being made.

There are a plurality of chambers 71 arranged which are preferably distributed evenly around the perimeter of the through opening 50 of the outer sleeve 5. In the present embodiment, eight chambers 71 are arranged such that each chamber is located approximately 45° from a neighboring chamber, but it is also possible to arrange more or less than eight chambers. The number of chambers preferably depends on the application. Preferably, each time the actuation element is rotated such that the spring-loaded ball moves from one chamber 71 and into a neighboring chamber 71, adjustable length strut is lengthened 1 mm. Each time the actuation element is rotated such that the spring-loaded ball moves from one chamber 71 and into a neighboring chamber 71, adjustable length strut may be lengthened between 0.1 mm to 1 mm.

It is important for the adjustable length strut to not be lengthened so easily or inadvertently such that accidental injury may be caused. Osteogenesis generally occurs over a considerable length of time and lengthening and/or angulation adjustment between adjacent bone fragments should only be done in a prescribed manner. Therefore, chambers 71 are preferably deep enough to securely house at least a portion of the spring loaded ball 70 and a spring constant k of the spring is sufficient enough to force the ball against side walls in the respective chambers such that preferably only intended actuation of the actuation unit causes the actuation unit to actuate.

With regard to the embodiment as shown in FIGS. 3 and 4, opening 72 can also be arranged in the outer sleeve 5 and that the chambers 71 can also be arranged in the actuation element 6. With such a configuration a same or similar result can preferably be achieved.

Figure 6:
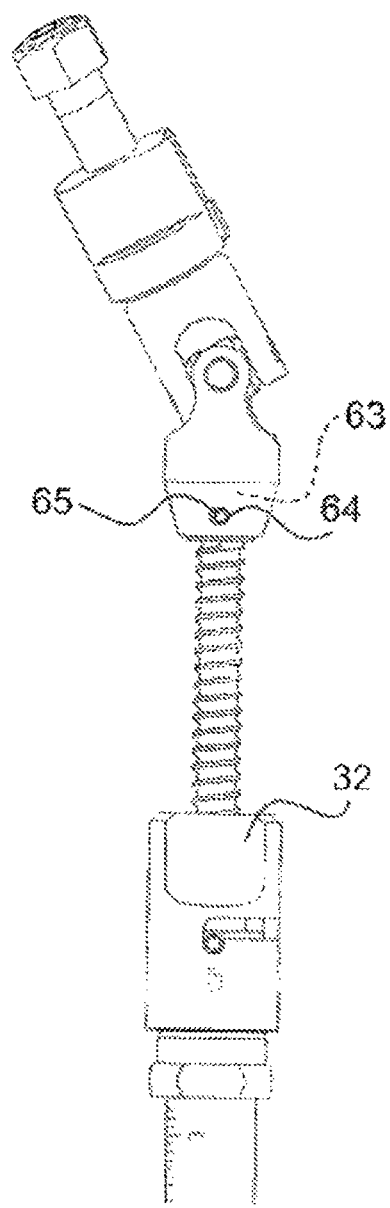
FIG. 6 shows a detailed view of FIG. 5.

The strut 3 with its end region is in a fixed connection with the actuation element 6. In the present embodiment, there is a Cardan (universal) joint 62 arranged between the strut 3 and the actuation element 6 in order to compensate angular differences between the strut 3 and the actuation element 6. Furthermore the actuation element 6 comprises an opening 63 in which the strut 3 extends as shown in FIG. 6. Preferably the strut 3 is in connection with the opening 63 by means of a thread, a press fit or any other suitable connection method which prevents a relative movement between the strut 3 and the actuation element 6. In case a thread is used, it is advantageous to secure the thread by means of a pin 64 which extends through the opening 63 and the strut 3. For that reason a pin opening 65 is arranged in the region of the opening 63. The use of a Cardan joint 62 has the advantage that adjustments can be made in advantageous manner, namely in a preferably precise and smooth manner.

Upon rotation of the actuation element 6, the strut will also be rotated and its length will be adjusted according to the degree of rotation. The feedback unit 7 then provides the user with an acoustic as well as with a haptic feedback due to its mechanical structure as outlined above.

Upon rotation of the actuation element 6, the strut will also be rotated and its length will be adjusted according to the degree of rotation. The feedback unit 7 then provides the user with an acoustic as well as with a haptic feedback due to its mechanical structure as outlined above.

The arrangement of the feedback unit 7 as mentioned herein has the advantage that in terms of dimension a very compact structure can be achieved. Thereby the overall weight can be significantly reduced and it is preferably more convenient for the patient to use such a structure.

As shown in FIG. 2, markings 67 showing the direction of rotation are arranged on an outer face of actuation unit 4 in order to allow the user to know in which direction actuation unit 4 is being actuated. In this region it is also possible to arrange a scale on which the user can visually recognize the amount of rotation, whereby a visual feedback can be provided.

Figure 5:
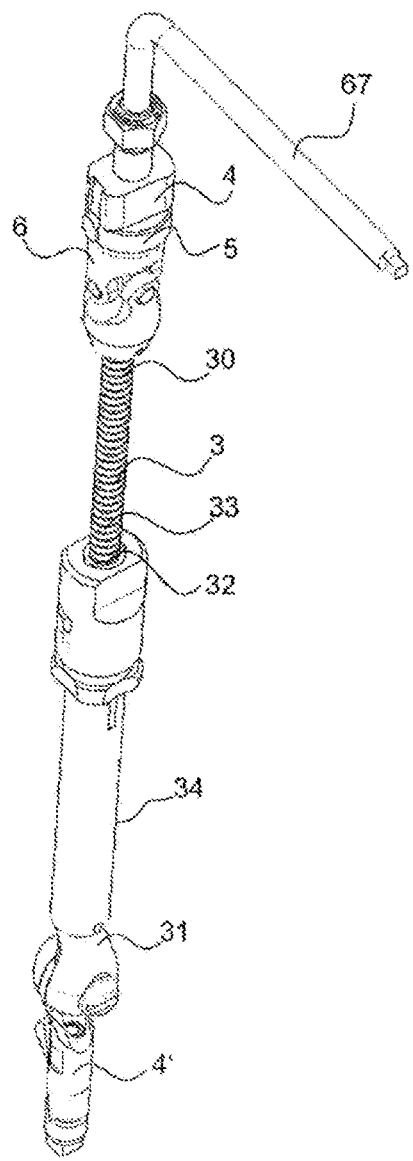
FIG. 5 shows the actuation unit of the previous figures in connection with an adjustable length strut to be used to connect two rings of the external fixator with each other.

FIGS. 5 and 6 show the strut 3 in connection with actuation unit 4 by way of its first end region 31 and with the clamping element 4' via its second end region 32. The clamping element 4' clamps the strut 3 in fixed manner to the fixation plate 1, 2 which is not shown here. The actuation unit 4 is also in a fixed connection with the respective fixation plate, but the actuation element 6 which is arranged within the actuation unit 4 is rotatable relative to the actuation unit 4. A rotation of the actuation element 6 preferably results in a rotation of the threaded strut 33 and in connection with the non-rotating strut section 34 such that the length of the strut 3 will be adjusted.

Figure 1B:
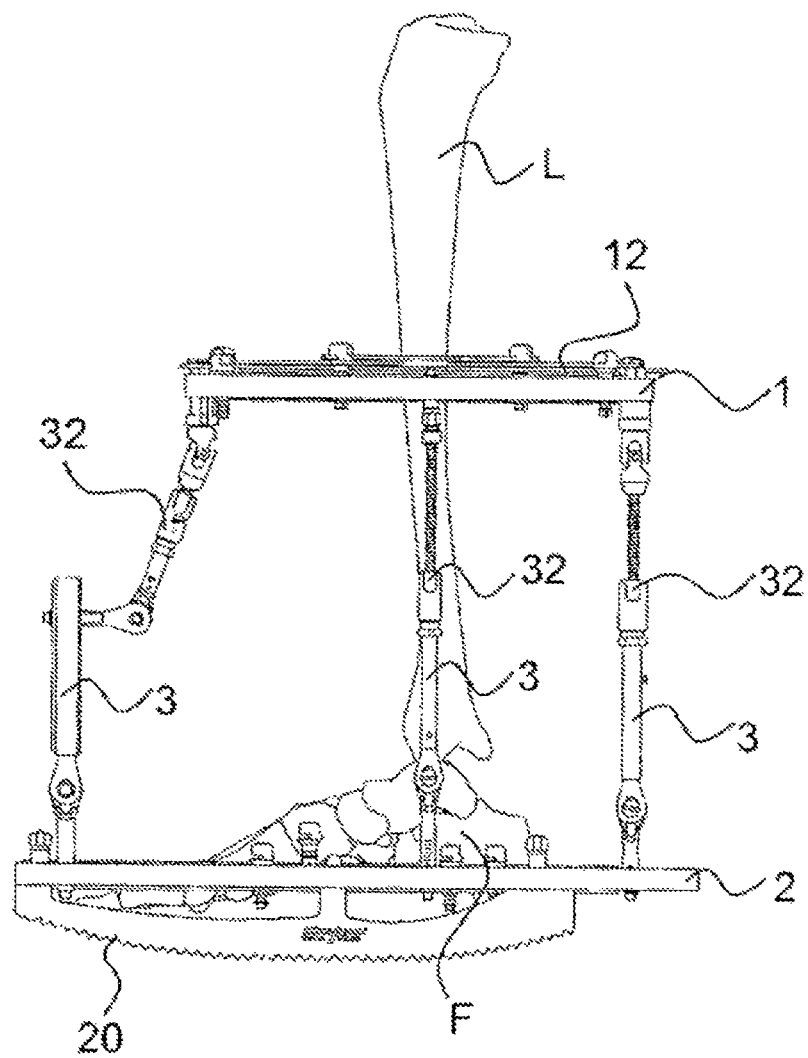
Figure 1C:
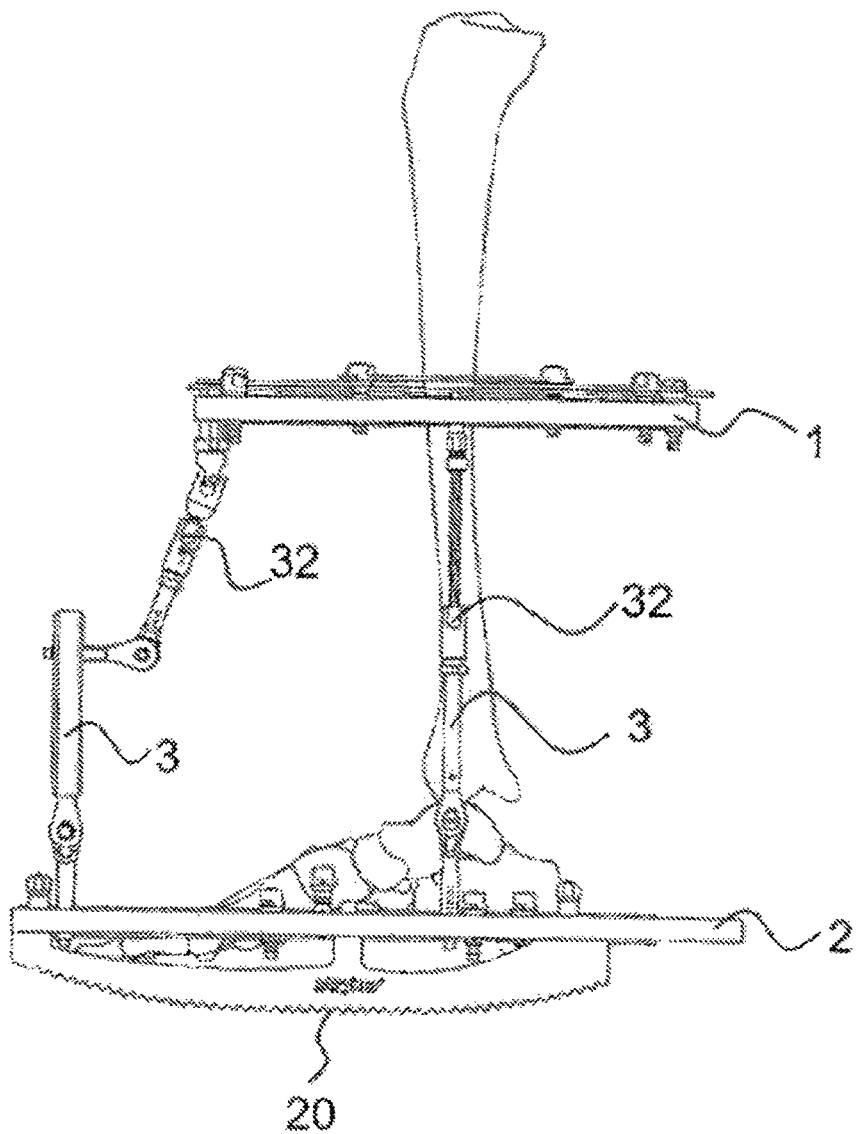
Figure 7:
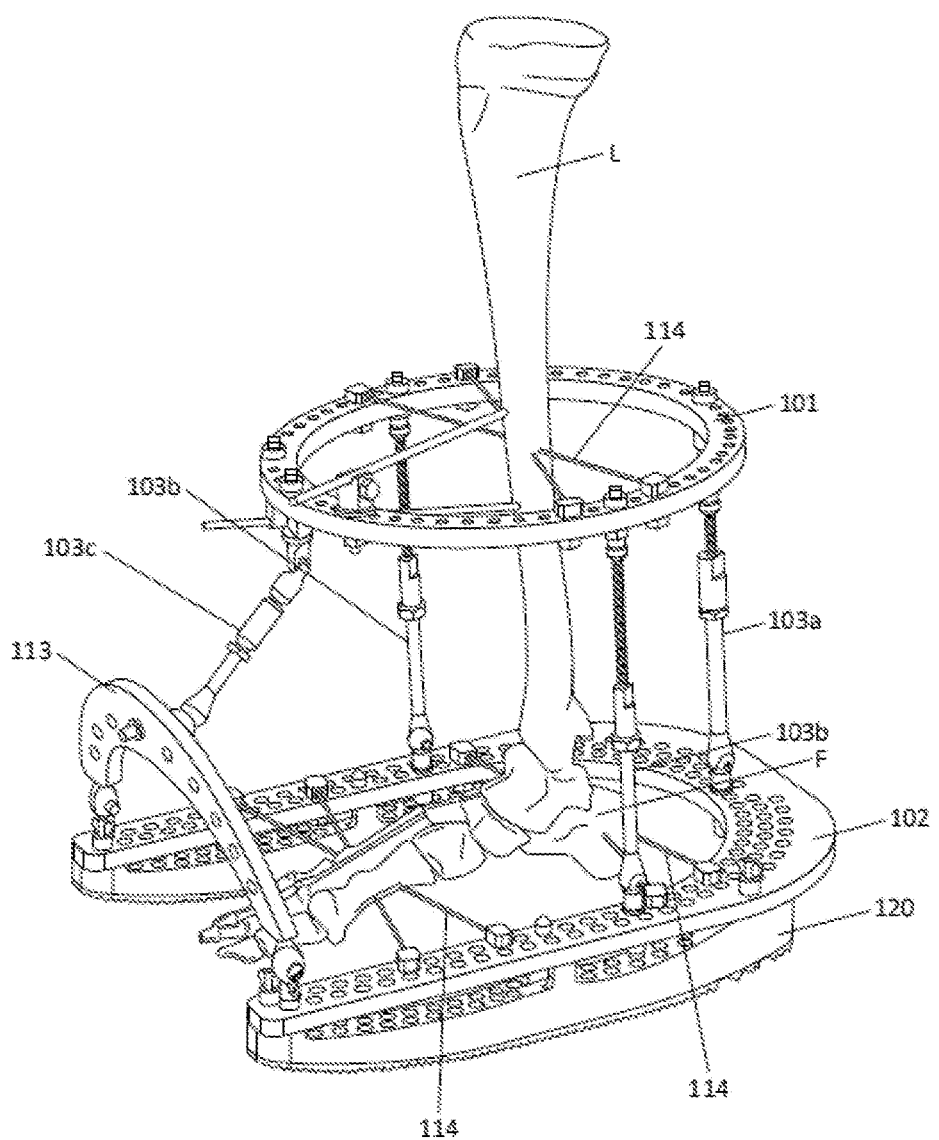
FIG. 7 shows a perspective view of an external fixation frame according to another embodiment of the invention.

FIG. 7 illustrates a perspective view an embodiment of an external fixator similar to that illustrated in FIGS. 1A-C. Similar parts are generally identified by a number 100 greater than the corresponding part identified in FIGS. 1A-C. FIG. 7 particularly illustrates a half-ring 113 hingedly coupled to the bottom fixation ring 102 and coupled to the top fixation ring 101 via half-ring strut 103c. Although the term half-ring is used, it should be understood that the half-ring is not limited to being half of a circular ring, but may take other shapes, preferably generally arcuate shapes. The top fixation ring 101 is further connected to the bottom fixation ring 102 with constrained hinge struts 103b and a universal hinge strut 103a.

As illustrated in FIG. 7, the half-ring 113 is coupled to the anterior part of the bottom fixation ring 102. Among other benefits, the half-ring 113 closes the open bottom fixation ring 102 such that the open bottom fixation ring does not deflect, or only minimally deflects, when fixation features, such as Kirschner wires ("K-wires") 114 are tensioned. Without half-ring 113, tensioning a member fixed at opposite ends of the open bottom fixation ring 102, such as a K-wire 114, may tend to cause the open portions of bottom fixation ring to deflect closer together. This deflection is limited by the rigid connection of the half-ring 113 to the bottom fixation ring 102.

Figure 8A:
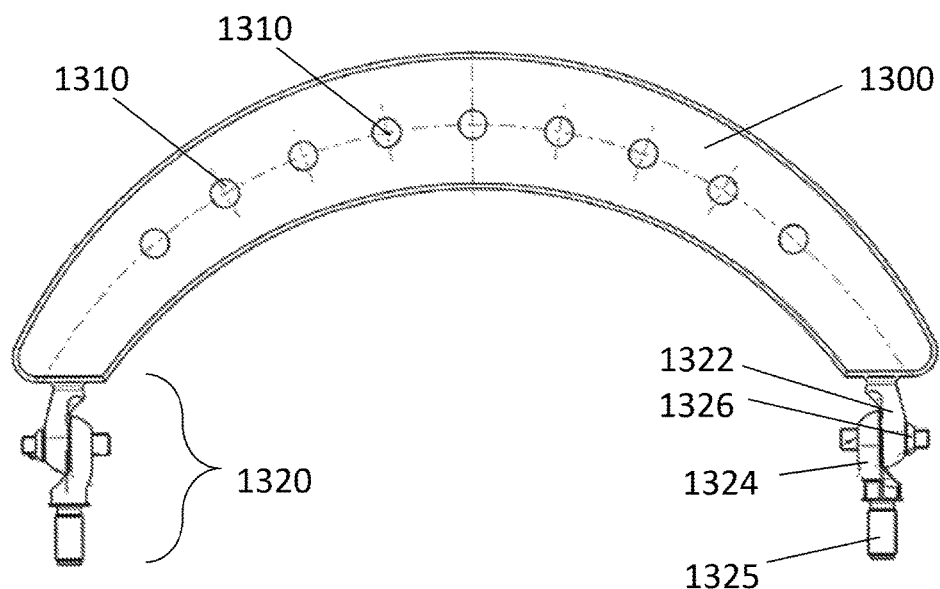
FIG. 8A shows a front plan view of a half-ring of the external fixation frame shown in FIG. 7.
Figure 8B:
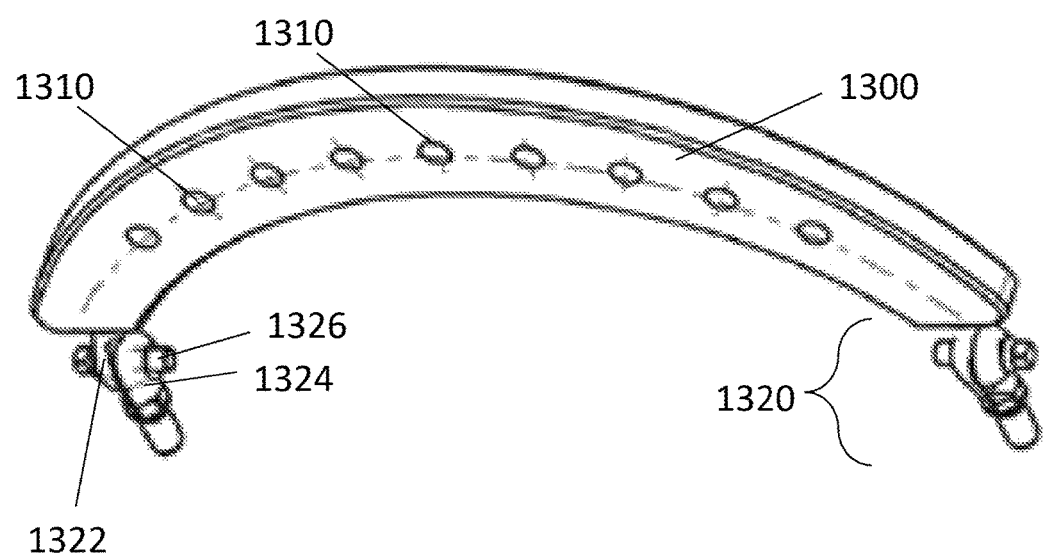
FIG. 8B shows a perspective view of the half-ring of FIG. 8A.
Figure 8C:
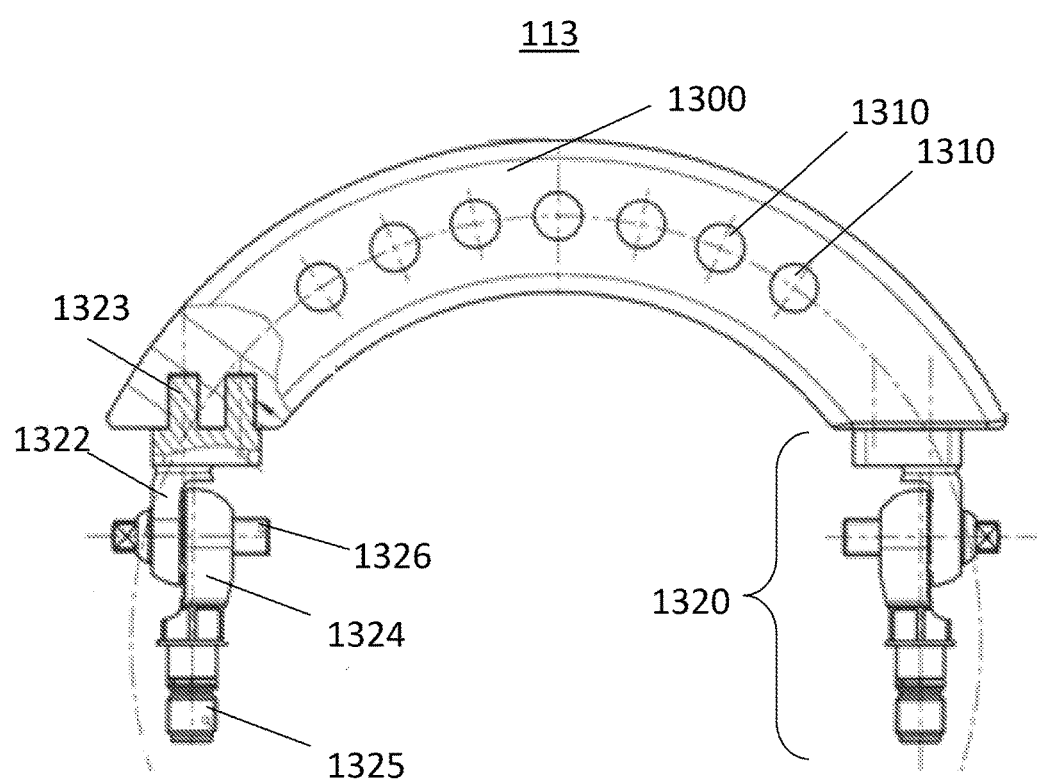
FIG. 8C shows a partial cross-sectional view of the half-ring of FIG. 8A.

The half-ring 113 is best illustrated in FIGS. 8A-C. The half-ring 113 may include a generally arcuate main portion 1300 similar to a portion of one of the fixation rings 101, 102. Similar to the fixation rings 101, 102, the half-ring 113 may include a number of openings 1310 to facilitate other members, such as half-ring strut 103c, to be attached to the half-ring.

The half-ring 113 may also include hinges 1320 at the ends of the main portion 1300. The hinges 1320 may include a first hinge portion 1322 and a second hinge portion 1324. The first hinge portion 1322 may be coupled to the half-ring 113, for example by an adhesive, or may alternately be integral with the half-ring. As illustrated in FIG. 8C, the first hinge portion 1322 may include a pronged connecting portion 1323 that mates with recesses in an end of the main portion 1300 of the half-ring 113. The fit may be a compression fit or a snap fit, or may otherwise be fixed, for example by an adhesive.

The first hinge portion 1322 may also include a textured surface and an aperture to accept a fastener. The aperture preferably is unthreaded. The fastener may be, for example, a screw 1326 with a first portion of the screw shaft unthreaded and a second portion of the screw shaft threaded. The second hinge portion 1324 may be of a generally similar structure to the first hinge portion 1322, having a textured surface and an aperture to accept a fastener. Preferably, the aperture is internally threaded.

The second hinge portion 1324 may also include a connecting portion 1325. The connecting portion 1325 may, for example, be cylindrical and configured to pass through an aperture 10 in the bottom fixation ring 2. The connecting portion 1325 may also be threaded to mate with a locking nut or other fastener to secure the second hinge portion 1324 in a fixed relation to the bottom fixation ring 2.

The screw 1326 may be inserted through the unthreaded aperture in the first hinge portion. Preferably the unthreaded aperture is large enough that the shaft of the screw 1326 can move freely through the aperture. The threaded portion of the screw 1326 is then inserted through the threaded aperture in the second hinge portion 1324. The threaded aperture is preferably dimensioned such that the screw 1326 must be rotated to pass through the threaded aperture. As the screw 1326 is rotated, the second hinge portion 1324 is drawn toward the first hinge portion 1322. When fully inserted, the unthreaded portion of the screw 1326 generally is located at the unthreaded aperture of the first hinge portion 1322 and the threaded portion of the screw is engaged with the threaded aperture of the second hinge portion 1324. In this position, the first hinge portion 1322 and second hinge portion 1324 are frictionally engaged such that rotation of the first hinge portion relative to the second hinge portion about the screw 1326 is resisted. In the embodiment in which one or both of the hinge portions 1322, 1324 include textured surfaces, such as ridges, the engagement of the textured surfaces may provide additional resistance against rotation. A nut may also be threaded onto any portion of the screw 1326 that extends beyond the aperture in the second hinge portion 1324 to help prevent unintentional rotation of the screw 1326 when in the fully threaded, locked position.

Figure 9A:
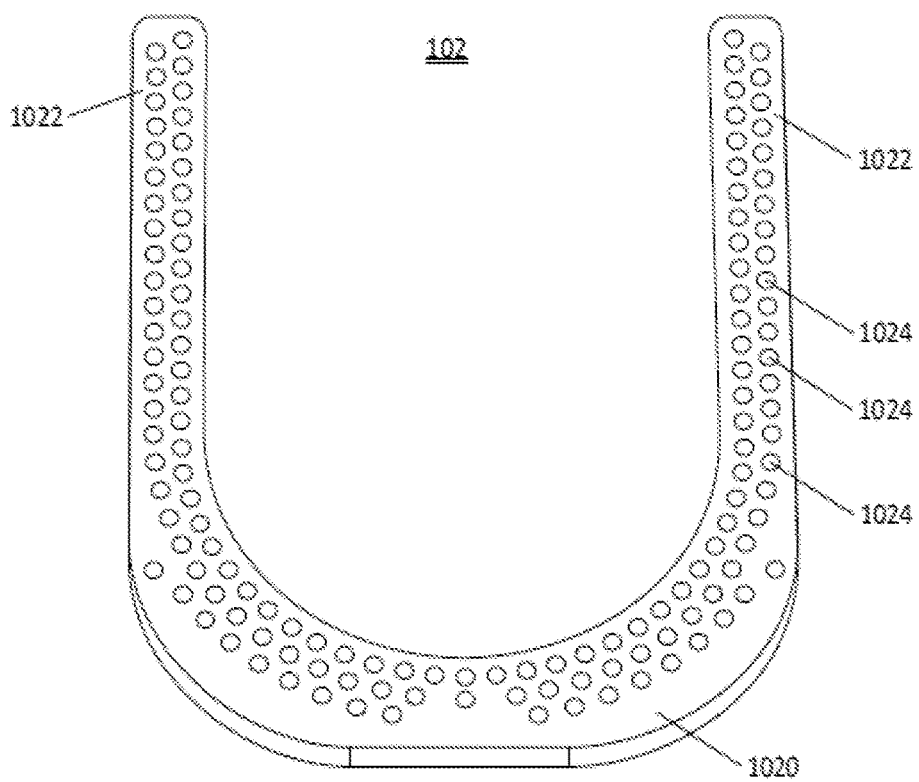
FIGS. 9A-B show top plan views of a bottom fixation ring of the external fixation frame shown in FIG. 7.
Figure 9B:
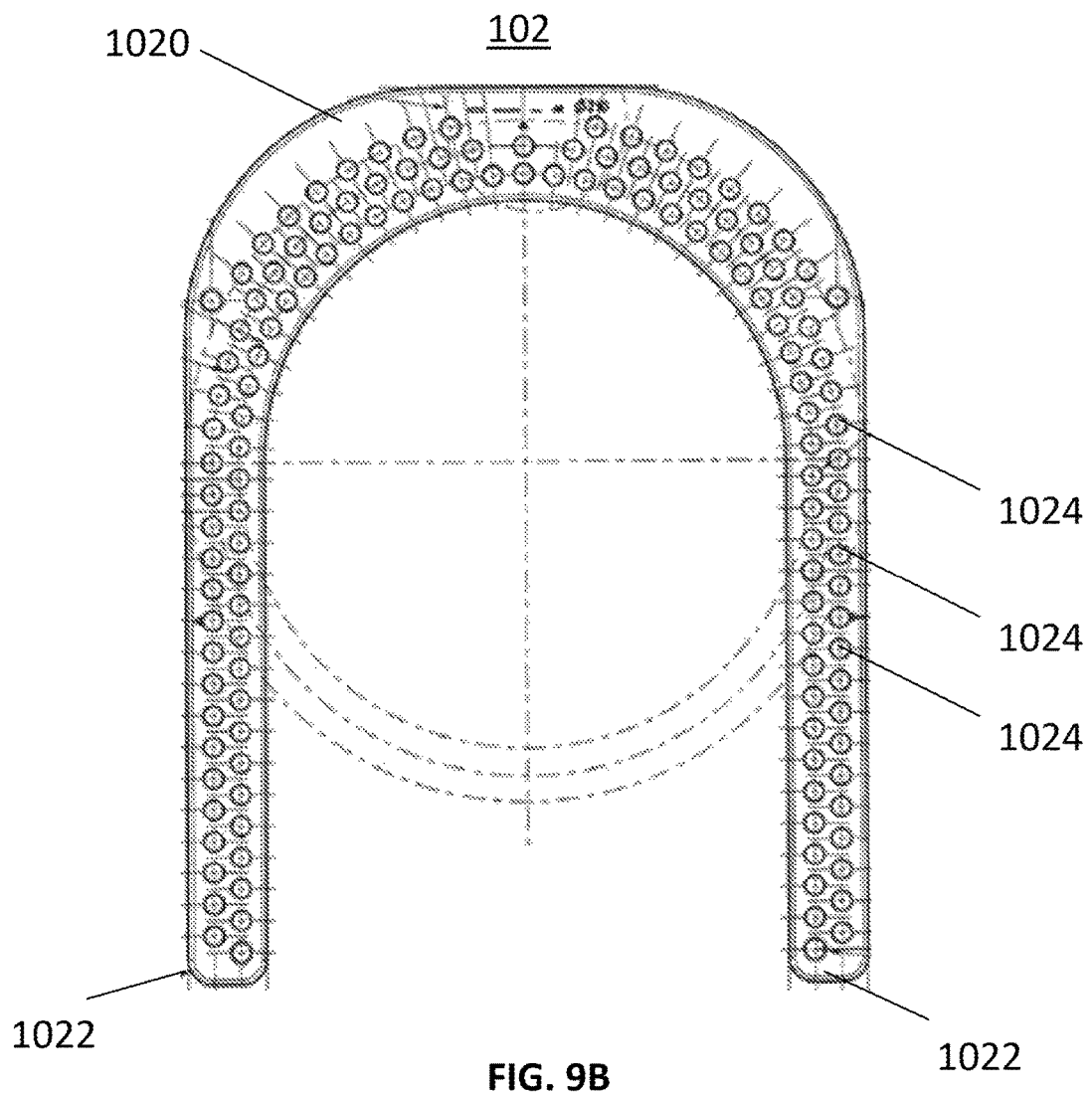

The bottom fixation ring 102 is illustrated in FIGS. 9A-B. The bottom fixation ring 102, in the particular embodiment shown, is generally "U" shaped with a posterior base 1020 and anterior projections 1022. The bottom fixation ring 102 may include a number of apertures or openings 1024 extending along the length of the bottom fixation ring. Although one particular pattern of openings 1024 is illustrated in FIG. 9, the number and placement of the openings 1024 is largely a matter of design choice. The openings 1024 may be used to connect components to the bottom fixation ring 102, such as a variety of struts and compression modules, as is explained in further detail below. Preferably, enough openings 1024 exist such that a surgeon or other user has a variety of choices in the placement of such components.

Rolling structure, or rocker 120, is illustrated in FIGS. 10A-F. Generally, rocker 120 has an elongate main body 1200 and an elongate ground-contacting rounded portion 1201. The ground-contacting rounded portion 1201 may include treads or other surface texture to increase friction with the ground. The ground-contacting rounded portion 1201 may be integral with the main body 1200, or may be otherwise coupled to the main body, for example by adhesive. The main body and ground-contacting rounded portion may include openings 1202 and 1203, respectively.

Figure 10A:
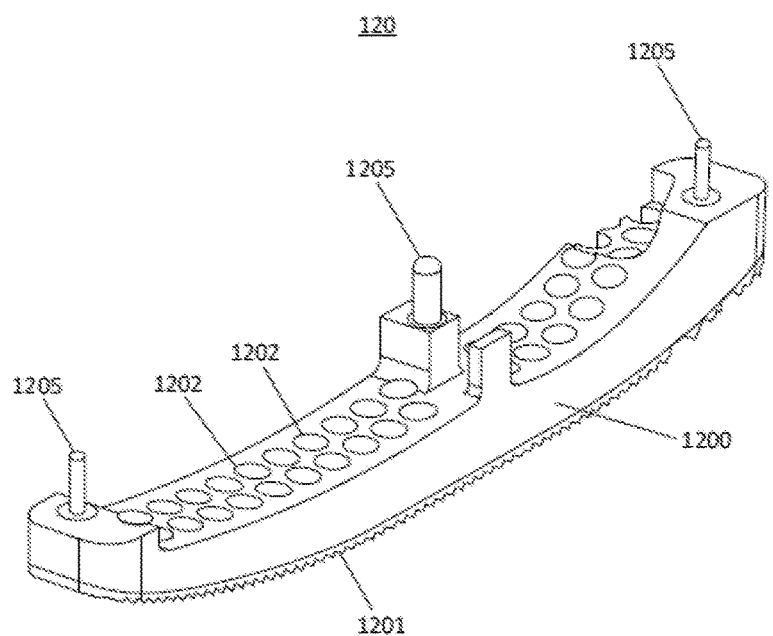
FIG. 10A shows a perspective view of a rocker shoe of the external fixation frame shown in FIG. 7.
Figure 10B:
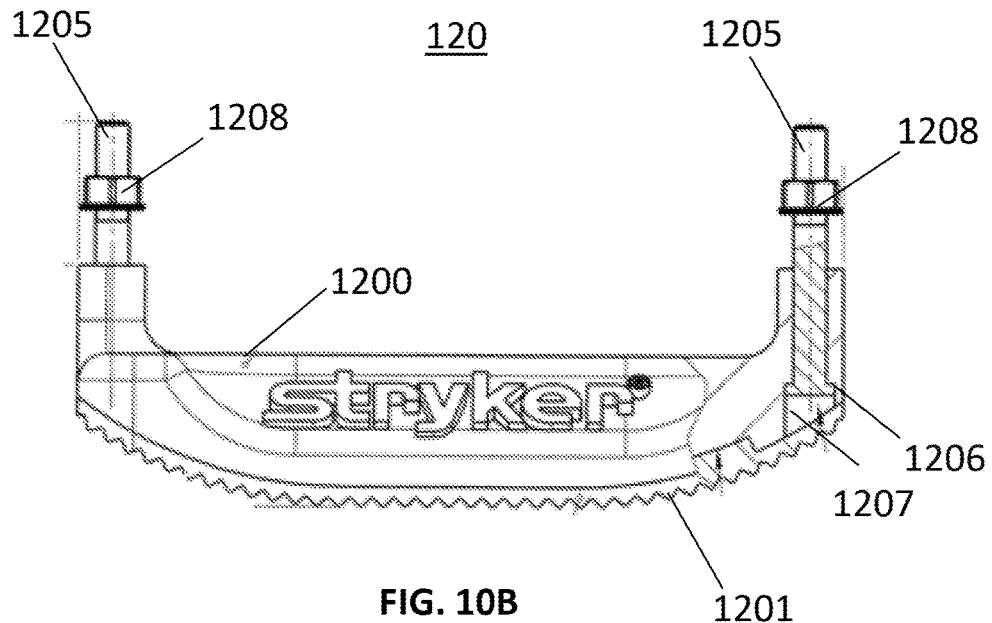
FIGS. 10B-D shows various plan views of the rocker shoe of FIG. 10A.
Figure 10C:
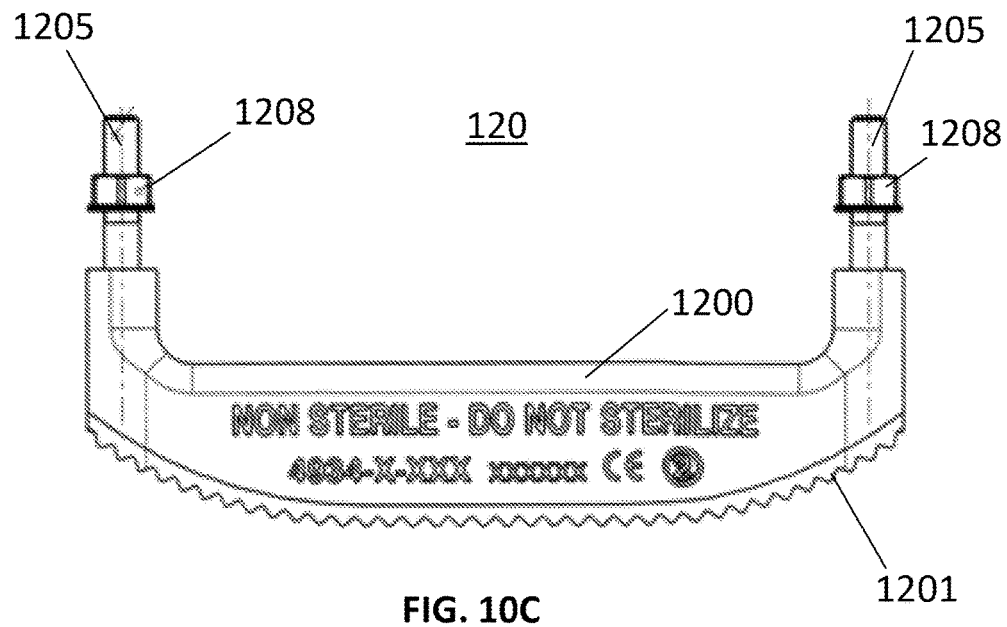
Figure 10D:
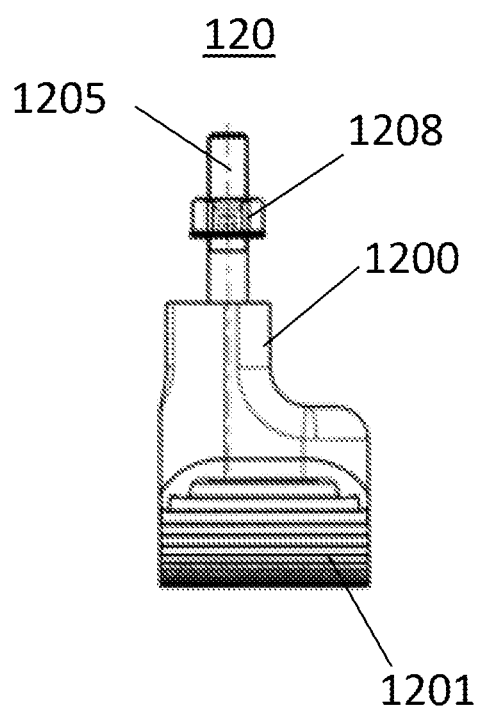
Figure 10E:
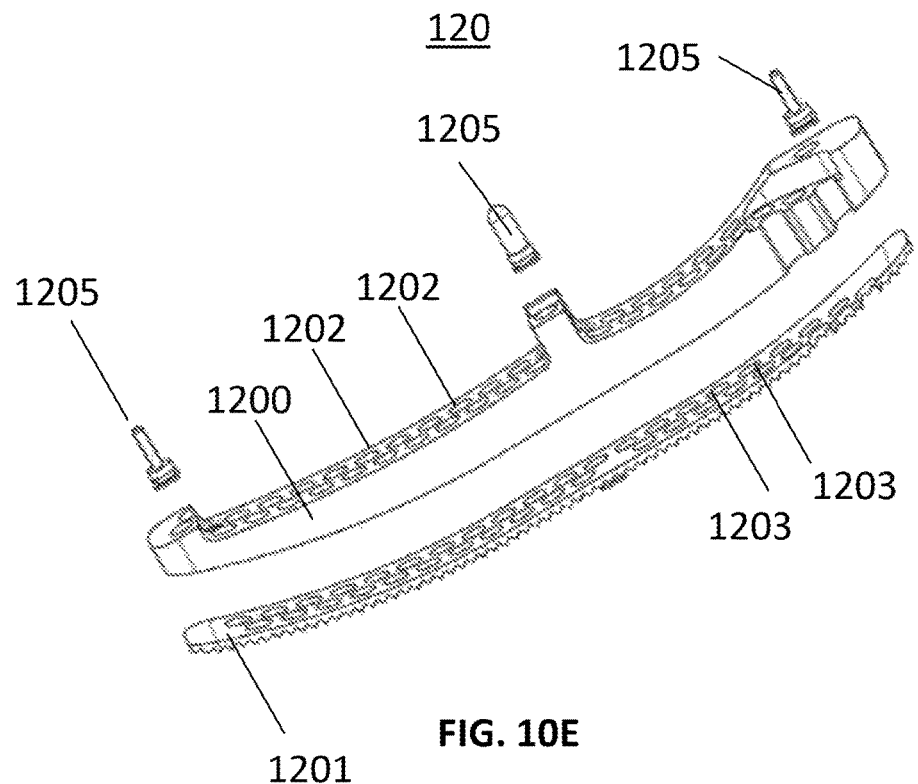
FIG. 10E shows an exploded view of the components of the rocker shoe of FIG. 10A.
Figure 10F:
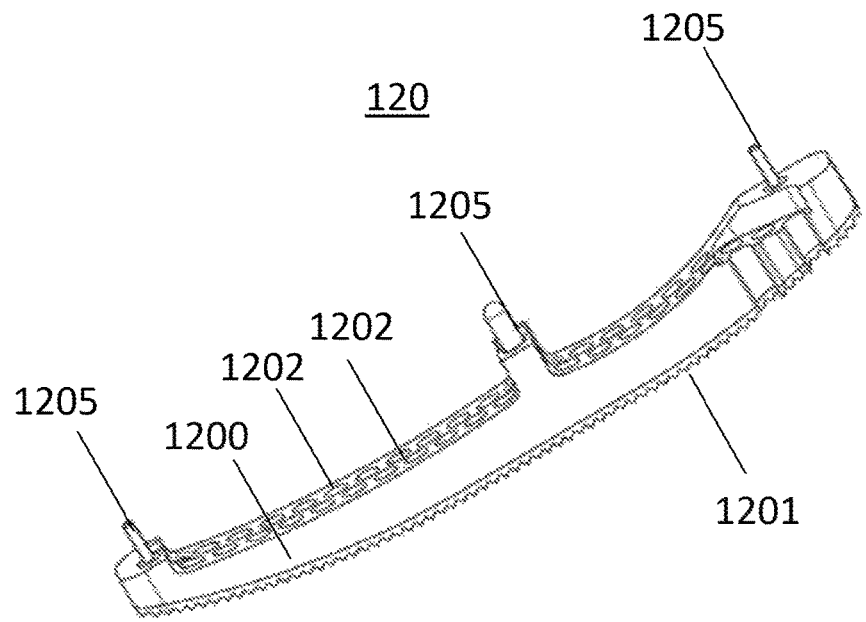
FIG. 10F shows a perspective view of the rocker shoe of FIG. 10E.
Figure 11A:
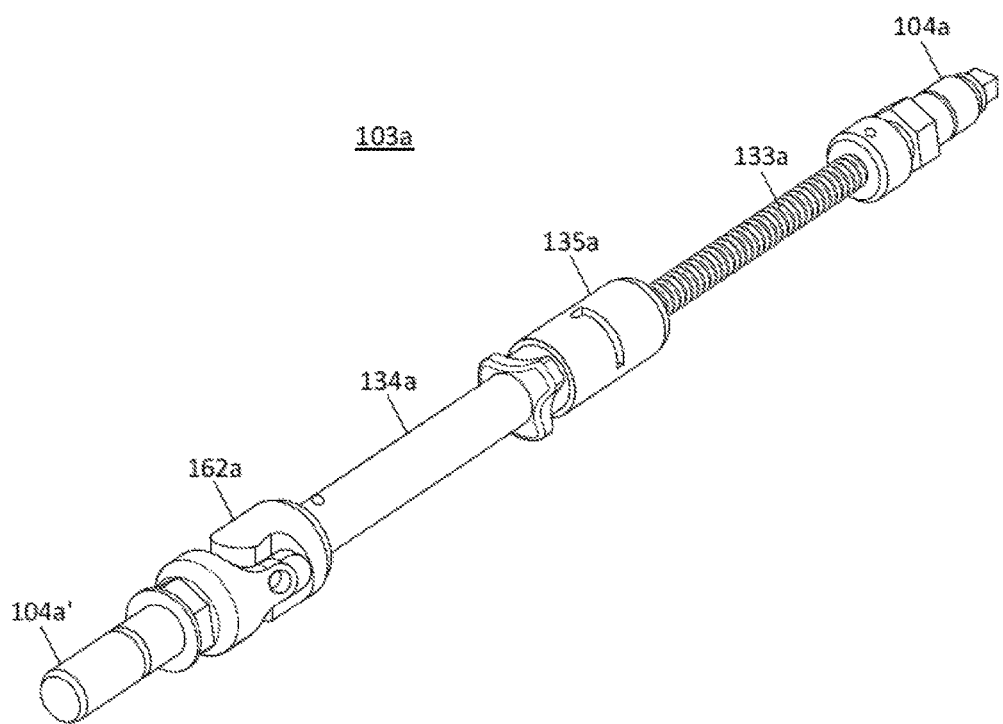
FIG. 11A shows a perspective view of a universal hinge strut of the external fixation frame shown in FIG. 7.
Figure 11B:
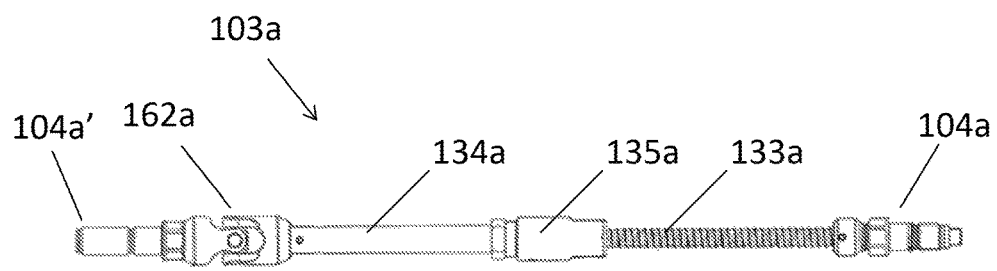
FIGS. 11B-D show various plan views of the universal hinge strut shown in FIG. 11A.
Figure 11C:
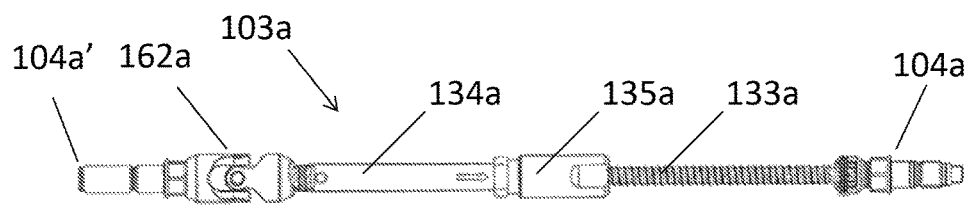
Figure 11D:
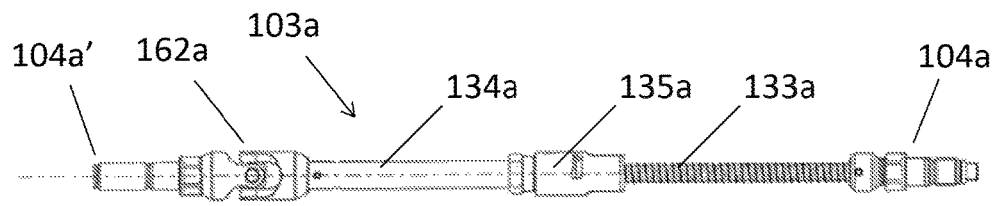
Figure 12A:
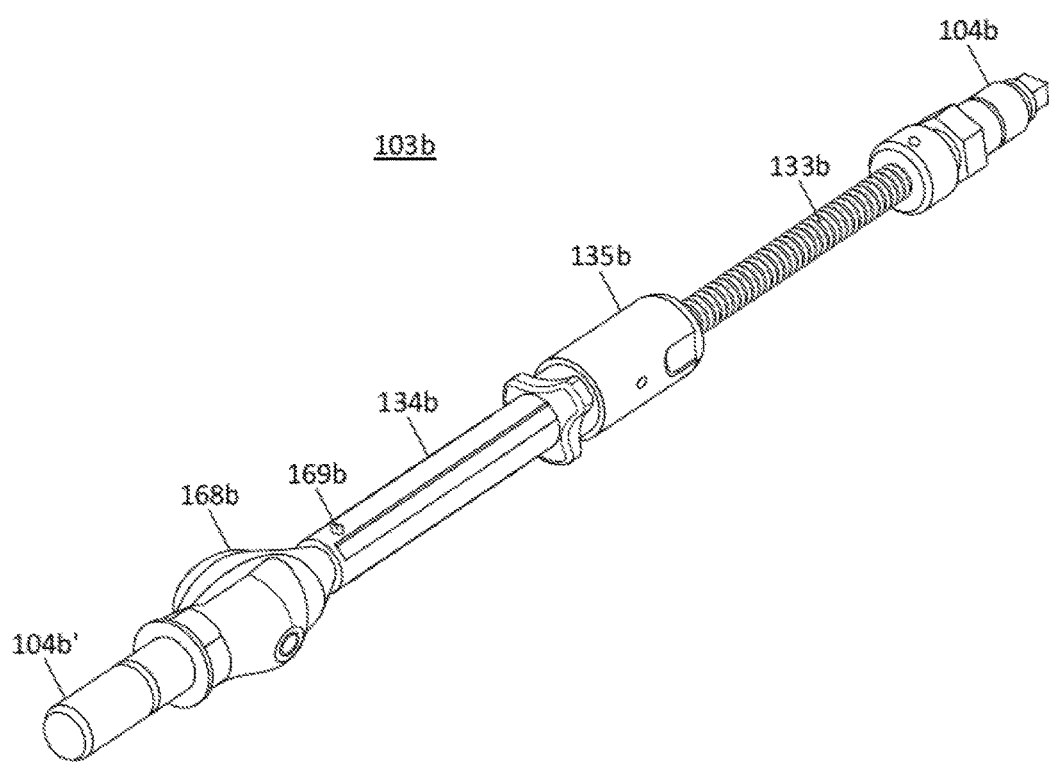
FIG. 12A shows a perspective view of a constrained hinge strut of the external fixation frame shown in FIG. 7.
Figure 12B:
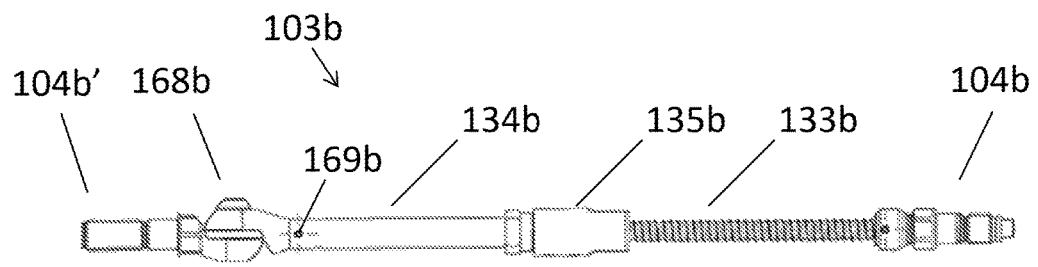
FIGS. 12B-D show various plan views of the constrained hinge strut shown in FIG. 12A.
Figure 12C:
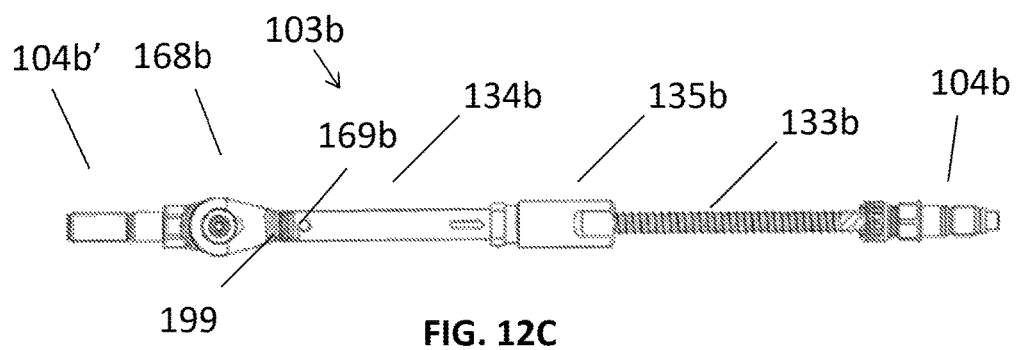
Figure 12D:
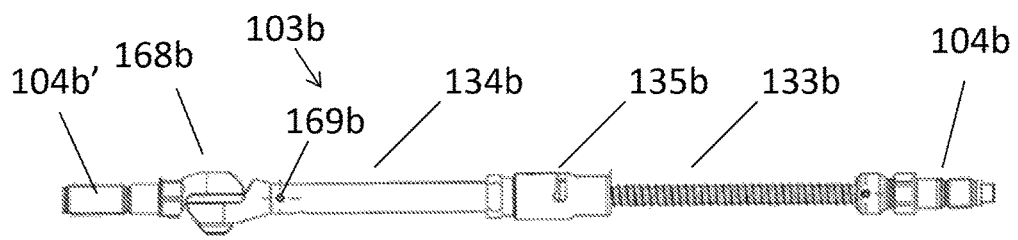
Figure 13A:
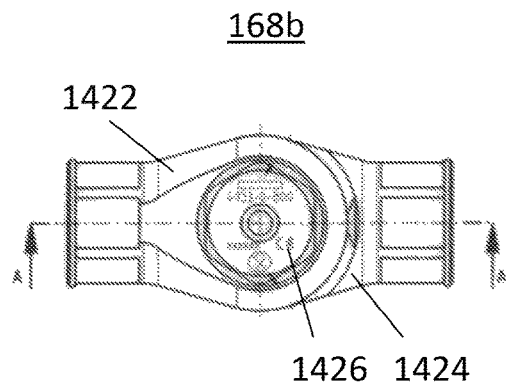
FIGS. 13A-D show various views of a constrained hinge joint of the constrained hinge strut shown in FIGS. 12A-D.
Figure 13B:
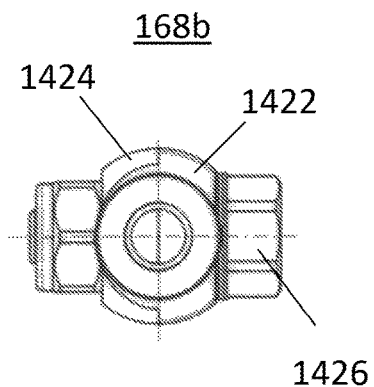
Figure 13C:
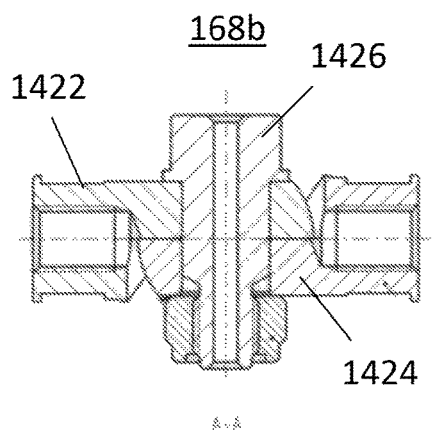
Figure 13D:
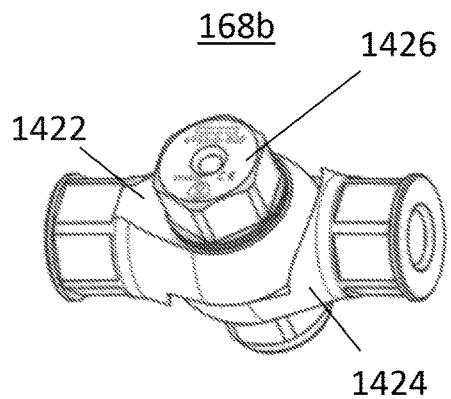

The main body 1200 of the rocker 120 may include one or more connecting pins 1205 (three connecting pins illustrated in FIGS. 10A and 10E-F, two connecting pins illustrated in FIGS. 10B-D). As best illustrated in FIG. 10B, the connecting pins 1205 may be generally cylindrical and dimensioned to securedly fit within an opening 1202 of the main body 1200. The bottom of the connecting pins 1205 may include a flange 1206 larger than the diameter of the opening 1202, such that the connecting pins 1205 cannot be pulled proximally through the rocker 120. A recess 1207 may be formed on a distal end of the main body 1200 where each connecting pin 1205 is located. The recess 1207 is formed such that the flange 1206 of the connecting pin 1205 is situated distal to the main body 1200 and proximal to the ground-contacting rounded portion 1201 of the rocker 120. The distal end of the connecting pins 1205 may be threaded and configured to fit through openings 1024 of the bottom fixation ring 102 to secure the rocker 120 to the bottom fixation ring. The distal end of the connecting pins 1205 may be threaded to accept a locking nut 1208 to lock the rocker 120 to the bottom fixation ring 102.

Although only one rocker 120 is illustrated in FIGS. 10A-F, it should be understood that two rockers would be used with the bottom fixation ring 102 to provide stable contact with the ground. Also, the rockers 120 may be identical, or may be similarly or symmetrically shaped. For example, as seen in FIG. 10D, the rocker 120 may include contours, which contours may be mirrored in a second rocker that is used with the bottom fixation ring.

As discussed above, multiple struts may be used to connect components of the fixation system and to allow for various types of movement and positioning between the components. In the illustrated embodiment, at least three different types of struts are used, including universal hinge struts 103a, constrained hinge struts 103b and half-ring struts 103c.

Now referring to FIGS. 11A-D, universal hinge strut 103a may be similar to the adjustable length strut 3 described above. In one embodiment, universal hinge strut 103a includes a length adjusting mechanism having a threaded strut 133a and a non-rotating strut 134a having an internal thread along at least a portion of a length thereof in which the threaded strut 133a engages. Universal hinge struts 103a may be connected to the upper fixation plate 101 by means of an actuation unit 104a and to the lower fixation plate 102 by means of a connecting element 104a'. It is also possible to use an actuation unit 104a to connect the universal hinge strut 103a to the upper fixation plate 101 as well as to the lower fixation plate 102. The actuation unit 104a is preferably provided to actuate the length-adjusting strut in order to adjust its length.

The actuation unit 104a may be substantially similar to the actuation unit 4 described above, including a ball and spring mechanism to provide auditory and/or tactile feedback. In the illustrated embodiment, universal hinge strut 103a includes a universal joint 162a near the connecting element 104a'. This is in contrast to the strut 3 described above, in which the universal joint 62 is positioned closer to the actuation element 4. The internal mechanisms described with relation to strut 3, however, generally apply with equal force to the universal hinge strut 103a. The universal hinge strut 103a may also include a quick-release mechanism 135a. Generally, the quick-release mechanism 135a has a locked position and an unlocked position. In the locked position, the threaded strut 133a can move into or out of the non-rotating strut 134a only by rotation of the threaded strut into the non-rotating strut. In the unlocked position, the threaded strut 133a may be moved into or out of the non-rotating strut 134a without rotation of the threaded strut, such that a user may quickly move the threaded strut into the non-rotating strut. This mechanism is more fully described in U.S. patent application Ser. No. 13/592,832, titled "Bone Transport External Fixation Frame."

Now referring to FIGS. 12A-D, constrained hinge struts 103b are nearly identical to universal hinge struts 103a, with a constrained hinge joint 168 rather than a universal hinge joint 162. The constrained hinge joints 168 allow for constrained rotation using a similar or identical mechanism as hinges 1320 of the half-ring 113. Similar to the universal hinge strut 103a, constrained hinge strut 103b includes a length adjusting mechanism having a threaded strut 133b and a non-rotating strut 134b having an internal thread along at least a portion of a length thereof in which the threaded strut 133b engages. Constrained hinge struts 103b may be connected to the upper fixation plate 101 by means of an actuation unit 104b and to the lower fixation plate 102 by means of a connecting element 104b'. It is also possible to use an actuation unit 104b to connect the constrained hinge strut 103b to the upper fixation plate 101 as well as to the lower fixation plate 102. The actuation unit 104b is preferably provided to actuate the length-adjusting strut in order to adjust its length.

The actuation unit 104b may be substantially similar to the actuation unit 4 described above, including a ball and spring mechanism to provide auditory and/or tactile feedback. In the illustrated embodiment, constrained hinge strut 103b includes a constrained joint 168b near the connecting element 104b'. The constrained hinge strut 103b may also include a quick-release mechanism 135b.

Constrained hinge joint 168 is shown in more detail in FIGS. 13A-D. The constrained hinge joint 168 may include a first hinge portion 1422 and a second hinge portion 1424. The first hinge portion 1422 may be coupled to non-rotating strut 134b. The second hinge portion 1424 may be coupled to the connecting portion 104b'.

The first hinge portion 1422 may also include a textured surface and an aperture to accept a fastener. The aperture preferably is unthreaded. The fastener may be, for example, a screw 1426 with a first portion of the screw shaft unthreaded and a second portion of the screw shaft threaded. The second hinge portion 1424 may be of a generally similar structure to the first hinge portion 1422, having a textured surface and an aperture to accept a fastener. Preferably, the aperture is internally threaded.

The screw 1426 may be inserted through the unthreaded aperture in the first hinge portion. Preferably the unthreaded aperture is large enough that the shaft of the screw 1426 can move freely through the aperture. The threaded portion of the screw 1426 is then inserted through the threaded aperture in the second hinge portion 1424. The threaded aperture is preferably dimensioned such that the screw 1426 must be rotated to pass through the threaded aperture. As the screw 1426 is rotated, the second hinge portion 1424 is drawn toward the first hinge portion 1422. When fully inserted, the unthreaded portion of the screw 1426 generally is located at the unthreaded aperture of the first hinge portion 1422 and the threaded portion of the screw is engaged with the threaded aperture of the second hinge portion 1424. In this position, the first hinge portion 1422 and second hinge portion 1424 are frictionally engaged such that rotation of the first hinge portion relative to the second hinge portion about the screw 1426 is resisted. In the embodiment in which one or both of the hinge portions 1422, 1424 include textured surfaces, such as ridges, the engagement of the textured surfaces may provide additional resistance against rotation. A nut may also be threaded onto any portion of the screw 1426 that extends beyond the aperture in the second hinge portion 1424 to help prevent unintentional rotation of the screw 1426 when in the fully threaded, locked position.

The constrained hinge strut 103b may also include an aperture 169b. The aperture 169b accepts a K-wire or other bone fastener that travels into the bone. The connection of the K-wire with the bone and the aperture 169b of the constrained hinge strut 103b lines the axis of the constrained hinge joint 168b with the anatomic joint axis.

Now referring back to FIG. 12C, in one embodiment, constrained hinge joint 168b is removably attached to non-rotating strut 134b by connection mechanism 199. Connection mechanism 199 may take any suitable form, such as a pin inserted through apertures, mating threads, snap fitting, press fitting, etc. In this embodiment, the particular joint, in this case a constrained hinge joint 168b, may be removed and replaced with a different type of joint, such as a universal hinge joint, polyaxial joint, or otherwise, depending on the particular requirement or desire. This interchangeability allows, for example, a less complex process if a user desires to change the way in which a particular strut is capable of moving.

Figure 14A:
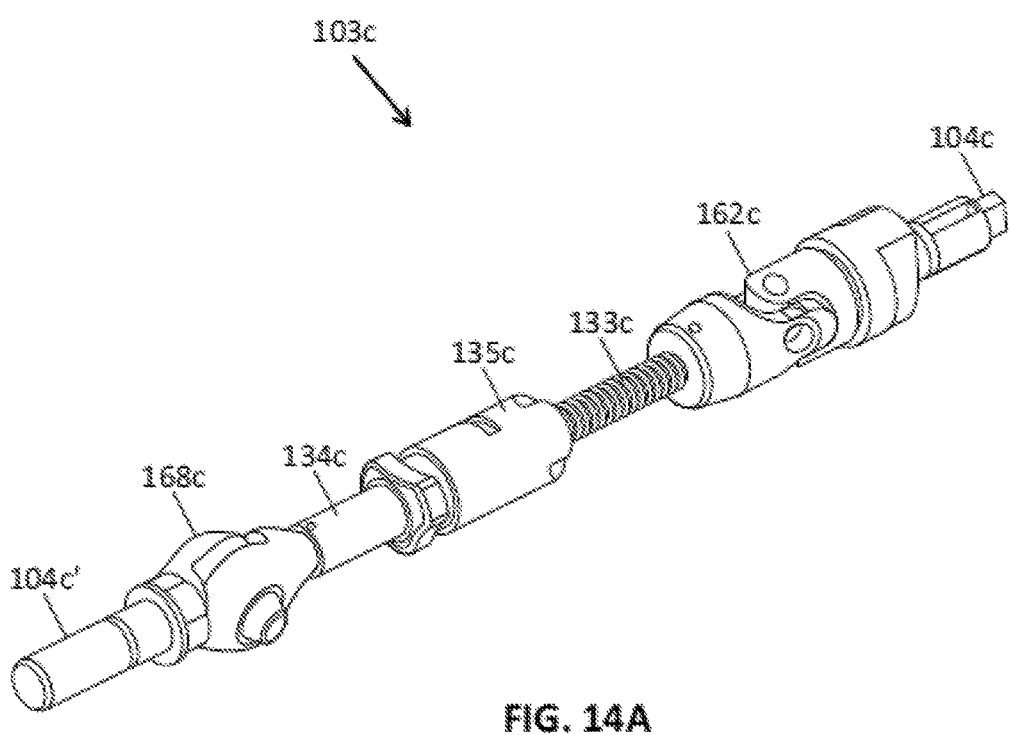
FIG. 14A shows a perspective view of one embodiment of a half-ring strut of the external fixation frame shown in FIG. 7.
Figure 14B:
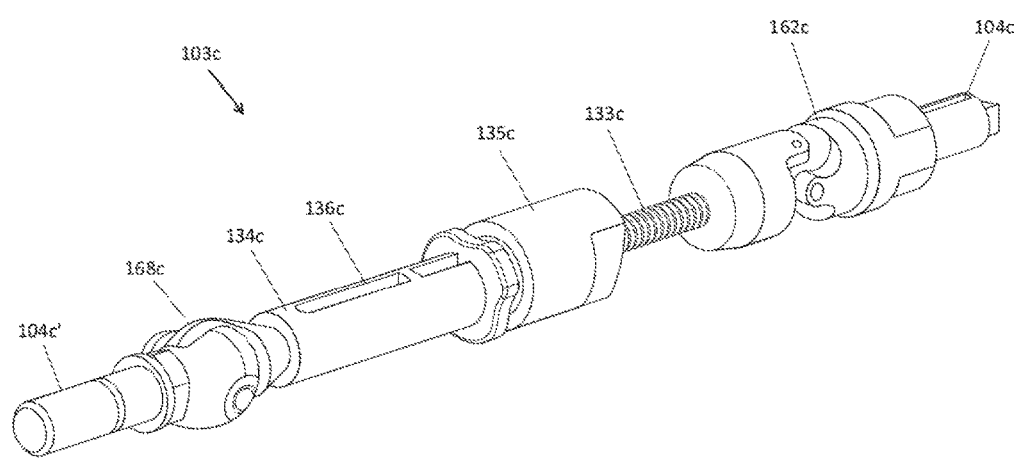
FIG. 14B shows a perspective view of another embodiment of a half-ring strut of the external fixation frame shown in FIG. 7.
Figure 14C:
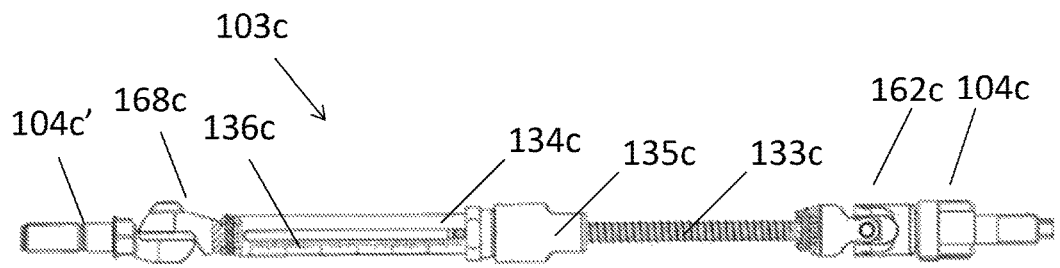
FIGS. 14C-E show various plan views of the half-ring strut shown in FIG. 14B.
Figure 14D:
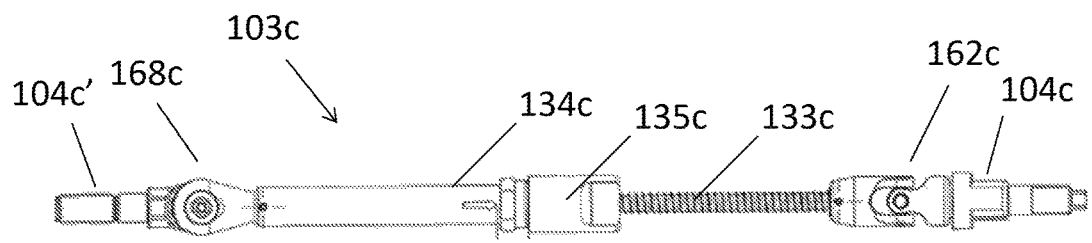
Figure 14E:
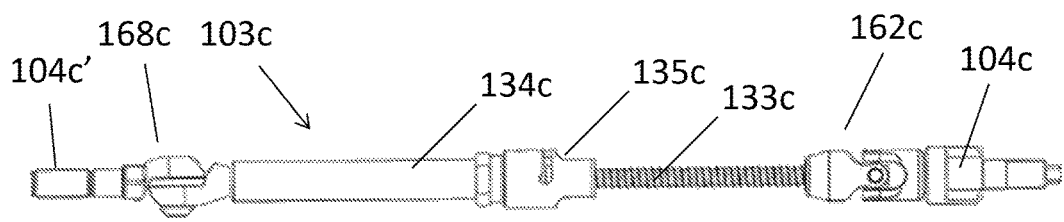

Now referring to FIG. 14A, half-ring strut 103c is illustrated. Half-ring strut 103c is substantially similar to universal hinge strut 103a and constrained hinge strut 103b, but includes both a universal joint 162c and a constrained joint 168c. The half-ring strut 103c may be used to fix upper fixation ring 101 to half-ring 113.

Half-ring strut 103c includes a length adjusting mechanism having a threaded strut 133c and a non-rotating strut 134c having an internal thread along at least a portion of a length thereof in which the threaded strut 133c engages. Half-ring strut 103c may be connected to the upper fixation plate 101 by means of an actuation unit 104c and to the half ring 113 by means of a connecting element 104c'. The actuation unit 104c is preferably provided to actuate the length-adjusting strut in order to adjust its length.

The actuation unit 104c may be substantially similar to the actuation unit 4 described above, including a ball and spring mechanism to provide auditory and/or tactile feedback. In the illustrated embodiment, half-ring strut 103c includes a constrained 168c near the connecting element 104c' and a universal joint 162c near the actuation unit 104c. The half-ring strut 103c may also include a quick-release mechanism 135c.

A similar embodiment of half-ring strut 103c is illustrated in FIGS. 14B-E, which also includes a scale 136c on the non-rotating strut 134c. The scale 136c includes indicia along a slot, the slot allowing a user to visualize how far the threaded strut 133c has advanced into the non-rotating strut 134c.

Figure 14F:
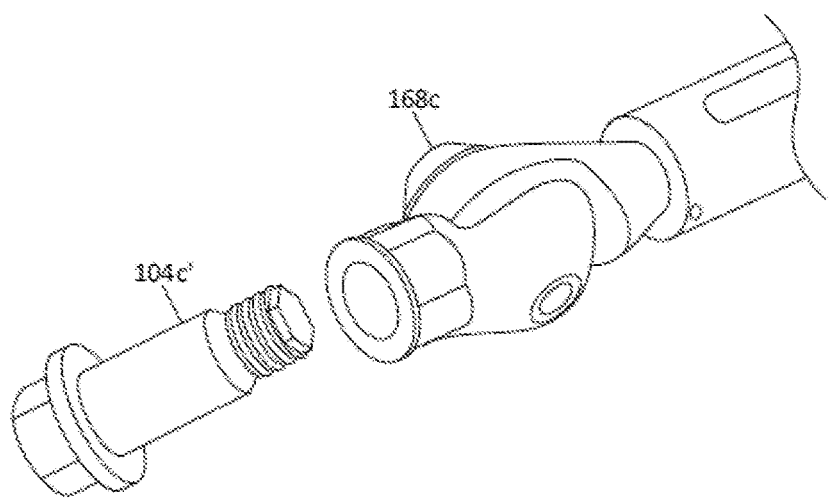
FIG. 14F shows an enlarged perspective partial view of a connecting element of the half-ring strut shown in FIGS. 14B-E.

FIG. 14F illustrates an enlarged view of the connecting element 104c' of the half-ring strut 103c. In the illustrated embodiment, the connecting element 104c' is bolt with external threading that mates with internal threading in a portion of the constrained joint 168c. The bolt includes a portion with a diameter larger than the diameter of a corresponding aperture in a fixation element, such as the half-ring 113. This connection may be accomplished by other mechanisms, for example using an internally threaded nut that threads onto the end of half-ring strut 103c. These mechanisms may apply with equal force to the other struts described herein.

In one embodiment of the fixation device, one universal hinge strut 103a fixes the top fixation plate 101 to the bottom fixation plate 102 at a posterior side of the device. Two constrained hinge joints 103b fix the top fixation plate 101 to the bottom fixation plate 102 at the medial and lateral sides of the device. A half-ring 113 is fixed at the anterior end of the bottom fixation plate 102, and a half-ring strut 103c fixes the half-ring 113 to an anterior portion of the top fixation plate 101. Each of the struts 103a-c may be increased or decreased in length as described above. The universal hinge strut 103a allows for top fixation ring 101 to move relative to the bottom fixation ring 102 with rotation about three axes. The constrained hinge strut 103b allows for the top fixation ring 101 to move relative to the bottom fixation ring 102 with rotation about a single axis. The half-ring 113 is constrained to rotation about one axis of rotation due to the hinges 1320 connecting the half-ring to the bottom fixation ring 102. The axis about which the half-ring rotates may be an axis that extends through the center of hinges 1320. The half-ring strut 103*c* allows the top fixation ring 101 to be rotated about three axes with respect to the half-ring 113, due to the universal joint 168*c* of the half-ring strut. This configuration allows the half-ring 113 to be assembled in multiple locations and positions on the distal portion of the foot ring, the half-ring having a lockable hinge. The combination of the features above allows for increased control of the foot and ankle in order to properly return it to an anatomic and functional position. The device also limits and/or avoids the possibility of changing of motor struts during treatment. In addition, the half-ring 113 provides added strength to the frame itself, as described above, by bridging the two free ends of the bottom fixation ring 102.

Figure 15:
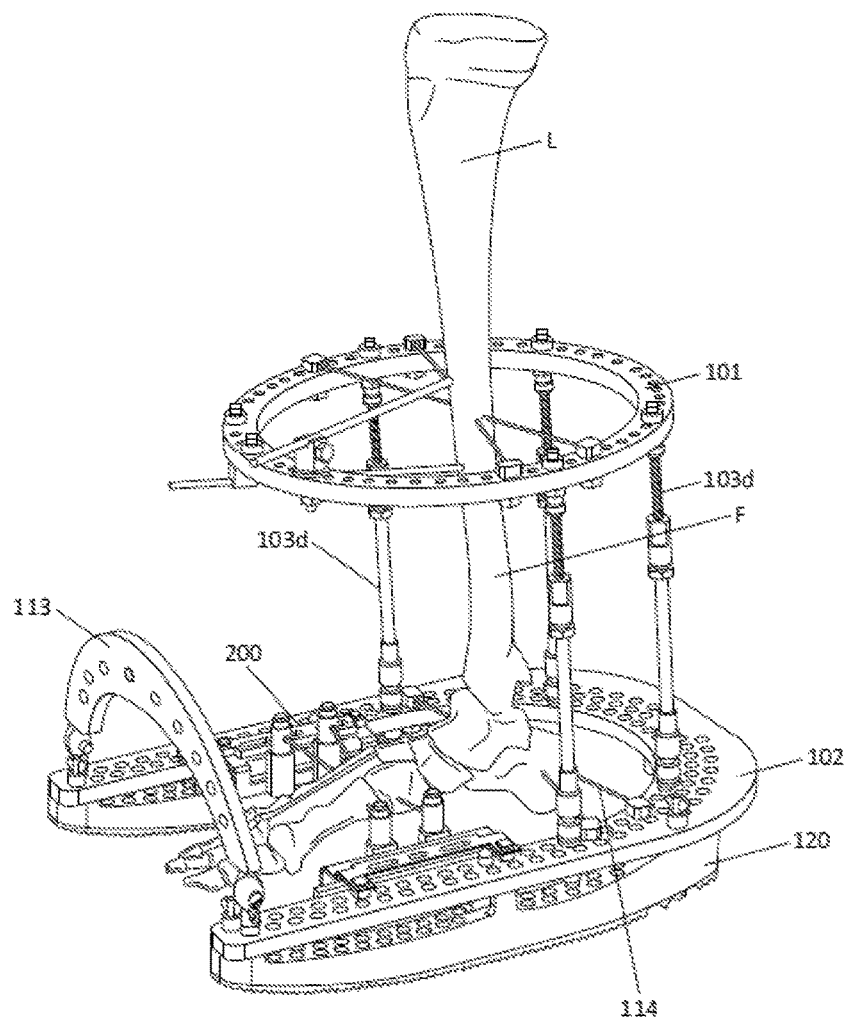
FIG. 15 is a perspective view of an alternate embodiment of an external fixator system.
Figure 16:
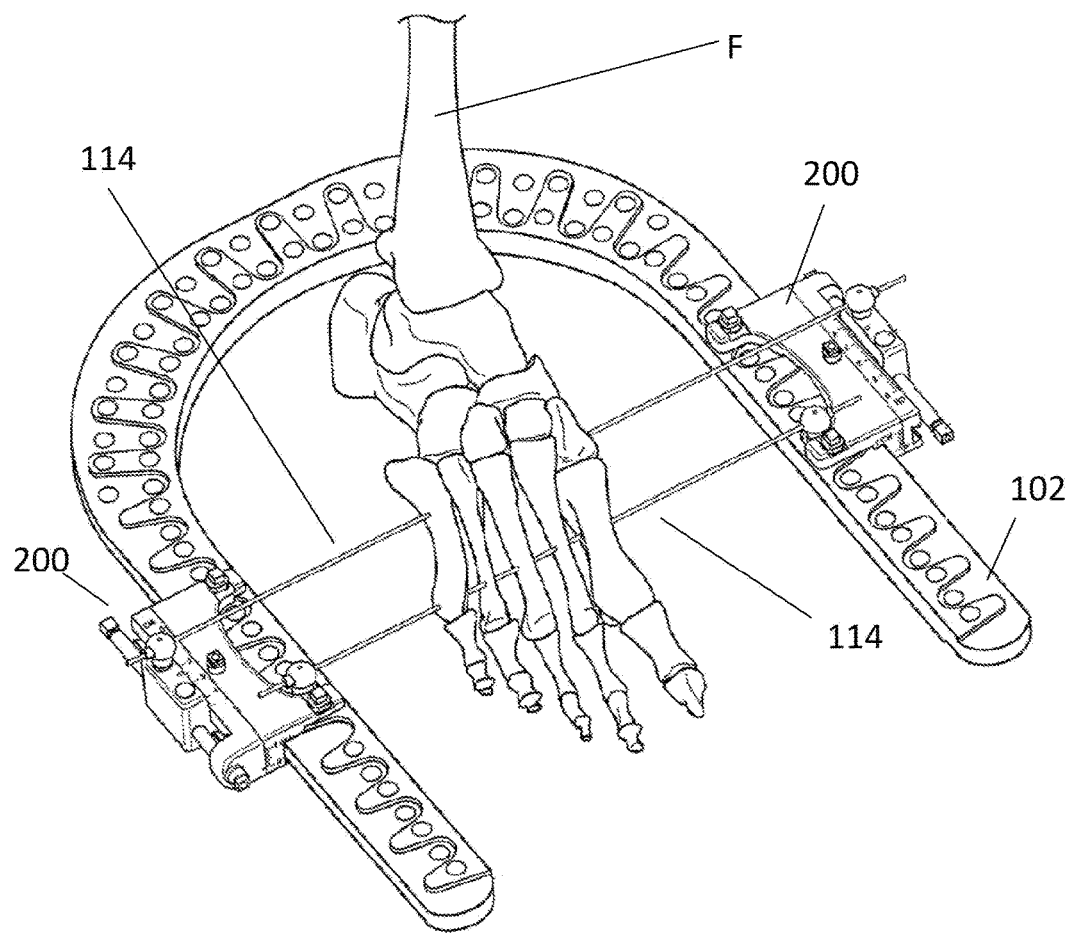
FIG. 16 is a perspective view of the bottom fixation ring and compression modules of the external fixator system of FIG. 15.

Now referring to FIG. 15, another embodiment of a foot fixation frame is illustrated. The illustrated embodiment is a static frame, using the same top and bottom fixation rings 101, 102 and half-ring strut 113 and rocker 120 as described previously. This embodiment, however, includes a different configuration of struts. Specifically, four or more struts 103*d* connect the top fixation ring 101 to the bottom fixation ring 102. By using four or more struts 103*d*, the rings 101 and 102 are over constrained and do not change positions relative to one another. As such, the struts 103*d* may be static struts. The struts 103*d* may also be any of those described previously, but kept in a locked position during the deformity correction. For example, a strut capable of polyaxial movement may be used for struts 103*d*. The strut may be angled initially when fixing top fixation ring 101 to bottom fixation ring 102 to provide for correct positioning, and then locked such that the strut 103*d* resists any additional repositioning.

The bottom fixation ring 102 may also include one or more foot compression modules 200, as illustrated in FIG. 15. Generally, the foot compression modules 200 are connected to the bottom fixation ring 102 and half pins or wires (e.g. K-wires 114) extend from a first compression module 200, through (or into) the foot F, and are fixed on the other side to the bottom fixation ring 102 or a second compression module 200. These compression modules 200 allow for controlled manipulation of the k-wires 114, and thus the bone fragments, during the deformity correction process. Compression modules are more fully described in U.S. Patent Publication No. 2011/0082458 and U.S. patent application Ser. No. 13/788,466 filed to Crozet et al., filed Mar. 7, 2013, and titled "Dynamic External Fixator and Methods for Use." The entire content of each of these applications is hereby incorporated by reference herein. As discussed above, when tensioning the K-wires 114, using the compression modules 200 or otherwise, the projecting ends of the bottom fixation ring 102 tend to deform because of the applied force and further because of the open shape of the bottom fixation ring. The inclusion of the half-ring 113, connected in the same way as described above, resists deformation during tensioning of K-wires 114.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For examples, components of one embodiment described herein may be combined with components of another embodiment described herein without departing from the scope of the invention.

The invention claimed is:

1. An external fixation frame for correcting a bone deformity, comprising:
   a top fixation ring;
   a u-shaped bottom fixation ring including a medial anterior projection, a lateral anterior projection, and a rounded posterior section connecting the medial anterior projection to the lateral anterior projection;
   a medial strut configured to couple a medial portion of the top fixation ring to a medial portion of the bottom fixation ring;
   a lateral strut configured to couple a lateral portion of the top fixation ring to a lateral portion of the bottom fixation ring;
   a half ring configured to couple to the bottom fixation ring so that it is positioned between the top fixation ring and the bottom fixation ring; and
   a rocker member configured to couple to a bottom surface of the bottom fixation ring.

2. The external fixation frame of claim 1, wherein the medial strut and the lateral strut each include a threaded rod.

3. The external fixation frame of claim 2, wherein the medial strut and the lateral strut are each an adjustable length telescopic strut that includes a cylindrical body portion configured to couple to the bottom fixation ring, the threaded rod coaxially received within the cylindrical body portion.

4. The external fixation frame of claim 2, wherein the medial strut and lateral strut each include a universal joint configured to couple to the bottom fixation ring.

5. The external fixation frame of claim 1, wherein the rocker member is configured to be positioned distal to the bottom fixation ring.

6. The external fixation frame of claim 5, wherein the rocker member includes a first rocker member portion configured to couple to the medial projection of the bottom fixation ring and a second rocker member portion configured to couple to the bottom surface of the lateral projection of the bottom fixation ring.

7. The external fixation frame of claim 6, wherein the first rocker member portion and the second rocker member portion are separate structures.

8. The external fixation frame of claim 6, wherein the first and second rocker member portions each include a ground contacting surface and a main body.

9. The external fixation frame of claim 8, wherein the first and second rocker member portions each include three cylindrical connecting members extending from the main body in a direction away from the ground contacting surface, the cylindrical connecting members configured to couple the first and second rocker member portions to the bottom fixation ring.

10. The external fixation frame of claim 9, wherein the cylindrical connecting members are adapted to be received within corresponding apertures in the bottom fixation ring.

11. The external fixation frame of claim 8, wherein the ground contacting surfaces are curved.

12. The external fixation frame if claim 8, wherein the ground contacting surfaces are textured.

13. The external fixation frame of claim 1, wherein the half ring has a first end portion and a second end portion connected by an arcuate portion.

14. The external fixation frame of claim 13, wherein the first end portion of the half ring is configured to couple to the medial anterior projection of the bottom fixation ring, and the second end portion of the half ring is configured to couple to the lateral anterior projection of the bottom fixation ring.

15. The external fixation frame of claim 14, further comprising a first bolt configured to couple the first end portion of the half ring to the medial anterior projection of the bottom fixation ring, and a second bolt configured to couple the second end portion of the half ring to the lateral anterior projection of the bottom fixation ring.

16. The external fixation frame of claim 15, wherein the first bolt and the second bolt include hinge members to allow for a hinged coupling of the half ring to the bottom fixation ring.

17. The external fixation frame of claim 1, further comprising:
- at least one bone fastener having a first end configured to operatively couple to the medial anterior projection of the bottom fixation ring and a second end configured to operably couple to the lateral anterior projection of the bottom fixation ring.

18. The external fixation frame of claim 1, further comprising two additional struts configured to couple the top fixation ring to the bottom fixation ring.

19. The external fixation frame of claim 1, wherein the half ring is configured to be directly connected to the bottom fixation ring but not to the top fixation ring.

20. The external fixation frame of claim 1, wherein the half ring has a shape of a half-circle.

* * * * *